(12) United States Patent
Measamer et al.

(10) Patent No.: US 9,936,949 B2
(45) Date of Patent: Apr. 10, 2018

(54) SURGICAL STAPLING INSTRUMENT WITH DRIVE ASSEMBLY HAVING TOGGLE FEATURES

(71) Applicant: Ethicon Endo-Surgery, Inc., Cincinnati, OH (US)

(72) Inventors: John P. Measamer, Cincinnati, OH (US); Christopher C. Miller, Loveland, OH (US); Brian F. DiNardo, Cincinnati, OH (US); Richard F. Schwemberger, Cincinnati, OH (US); Johnny H. Alexander, III, West Chester, OH (US)

(73) Assignee: Ethicon LLC, Guaynabo, PR (US)

( * ) Notice: Subject to any disclaimer, the term of this patent is extended or adjusted under 35 U.S.C. 154(b) by 860 days.

(21) Appl. No.: 14/033,709

(22) Filed: Sep. 23, 2013

(65) Prior Publication Data

US 2015/0083773 A1 Mar. 26, 2015

(51) Int. Cl.
*A61B 17/04* (2006.01)
*A61B 17/10* (2006.01)
(Continued)

(52) U.S. Cl.
CPC ........ *A61B 17/068* (2013.01); *A61B 17/1155* (2013.01); *A61B 2017/00398* (2013.01);
(Continued)

(58) Field of Classification Search
CPC .............. A61B 17/072; A61B 17/1285; A61B 2017/2923; A61B 2017/2943
(Continued)

(56) References Cited

U.S. PATENT DOCUMENTS 4,805,823 A 2/1989 Rothfuss
5,205,459 A 4/1993 Brinkerhoff et al.
(Continued)

FOREIGN PATENT DOCUMENTS

CN 201328851 Y 10/2009
CN 102512222 A 6/2012
EP 2 140 817 A1 1/2017

OTHER PUBLICATIONS

U.S. Appl. No. 13/688,951, filed Nov. 29, 2012.
(Continued)

*Primary Examiner* — Hemant M Desai
*Assistant Examiner* — Eyamindae Jallow
(74) *Attorney, Agent, or Firm* — Frost Brown Todd LLC

(57) ABSTRACT

An apparatus includes an end effector, a shaft assembly including a translating drive member, and a drive assembly. The end effector includes a distally advancing cutting member and staple driver. The translating drive member is operable to actuate the end effector. The drive assembly is in communication with the translating drive member and includes a motor, a rotary drive member, a first link, and at least one toggle link. The rotary drive member is in communication with the motor. The first link is in communication with the rotary drive member. The at least one toggle link is in communication with the first link and the translating drive member. The rotary drive member is operable to convey linear motion to the first link. The first link is able to convey linear motion to the translating drive member.

20 Claims, 13 Drawing Sheets

(51) Int. Cl.
*A61B 17/068* (2006.01)
*A61B 17/115* (2006.01)
A61B 17/00 (2006.01)
A61B 17/29 (2006.01)

(52) U.S. Cl.
CPC ............... *A61B 2017/2913* (2013.01); *A61B 2017/2922* (2013.01)

(58) Field of Classification Search
USPC ...................................................... 227/175.1
See application file for complete search history.

(56) References Cited

U.S. PATENT DOCUMENTS

| | | | |
|---|---|---|---|
| 5,271,544 A | 12/1993 | Fox et al. | |
| 5,275,322 A | 1/1994 | Brinkerhoff et al. | |
| 5,285,945 A | 2/1994 | Brinkerhoff et al. | |
| 5,292,053 A | 3/1994 | Bilotti et al. | |
| 5,333,773 A | 8/1994 | Main et al. | |
| 5,350,104 A | 9/1994 | Main et al. | |
| 5,415,334 A | 5/1995 | Williamson, IV et al. | |
| 5,465,895 A | 11/1995 | Knodel et al. | |
| 5,467,911 A * | 11/1995 | Tsuruta ............... | A61B 17/0682 227/175.1 |
| 5,533,661 A | 7/1996 | Main et al. | |
| 5,540,375 A | 7/1996 | Bolanos et al. | |
| 5,597,107 A | 1/1997 | Knodel et al. | |
| 5,632,432 A | 5/1997 | Schulze et al. | |
| 5,673,840 A | 10/1997 | Schulze et al. | |
| 5,704,534 A | 1/1998 | Huitema et al. | |
| 5,814,055 A | 9/1998 | Knodel et al. | |
| 6,945,444 B2 | 9/2005 | Gresham et al. | |
| 6,978,921 B2 | 12/2005 | Shelton, IV et al. | |
| 7,000,818 B2 | 2/2006 | Shelton, IV et al. | |
| 7,143,923 B2 | 12/2006 | Shelton, IV et al. | |
| 7,303,108 B2 | 12/2007 | Shelton, IV et al. | |
| 7,367,485 B2 | 5/2008 | Shelton, IV et al. | |
| 7,380,695 B2 | 6/2008 | Doll et al. | |
| 7,380,696 B2 | 6/2008 | Shelton, IV et al. | |
| 7,404,508 B2 | 7/2008 | Smith et al. | |
| 7,434,715 B2 | 10/2008 | Shelton, IV et al. | |
| 7,464,849 B2 | 12/2008 | Shelton, IV et al. | |
| 7,721,930 B2 | 5/2010 | McKenna et al. | |
| 7,794,475 B2 | 9/2010 | Hess et al. | |
| 7,959,050 B2 | 6/2011 | Smith et al. | |
| 8,393,516 B2 | 3/2013 | Kostrzewski | |
| 8,408,439 B2 | 4/2013 | Huang et al. | |
| 8,453,914 B2 | 6/2013 | Laurent et al. | |
| 9,463,022 B2 | 10/2016 | Swayze et al. | |
| 2010/0213240 A1* | 8/2010 | Kostrzewski ........ | A61B 17/072 227/180.1 |
| 2011/0295295 A1* | 12/2011 | Shelton, IV ......... | A61B 17/072 606/170 |
| 2012/0116379 A1 | 5/2012 | Yates et al. | |
| 2012/0292372 A1 | 11/2012 | Nalagatla et al. | |

OTHER PUBLICATIONS

U.S. Appl. No. 13/688,992, filed Nov. 29, 2012.
U.S. Appl. No. 13/693,430, filed Dec. 4, 2012.
U.S. Appl. No. 13/693,455, filed Dec. 4, 2012.
U.S. Appl. No. 13/706,827, filed Dec. 6, 2012.
U.S. Appl. No. 13/716,313, filed Dec. 17, 2012.
U.S. Appl. No. 13/716,318, filed Dec. 17, 2012.
U.S. Appl. No. 13/716,323, filed Dec. 17, 2012.
U.S. Appl. No. 14/033,688, filed Sep. 23, 2013.
U.S. Appl. No. 14/033,751, filed Sep. 23, 2013.
U.S. Appl. No. 14/033,763, filed Sep. 23, 2013.
European Search Report and Written Opinion dated Dec. 9, 2014 for Application 14185801.9, 10 pgs.
International Search Report and Written Opinion dated Dec. 10, 2014 for Application PCT/US2014/056518, 16 pgs.
Chinese Office Action dated Jan. 22, 2018 for Application No. 2014800521558.

* cited by examiner

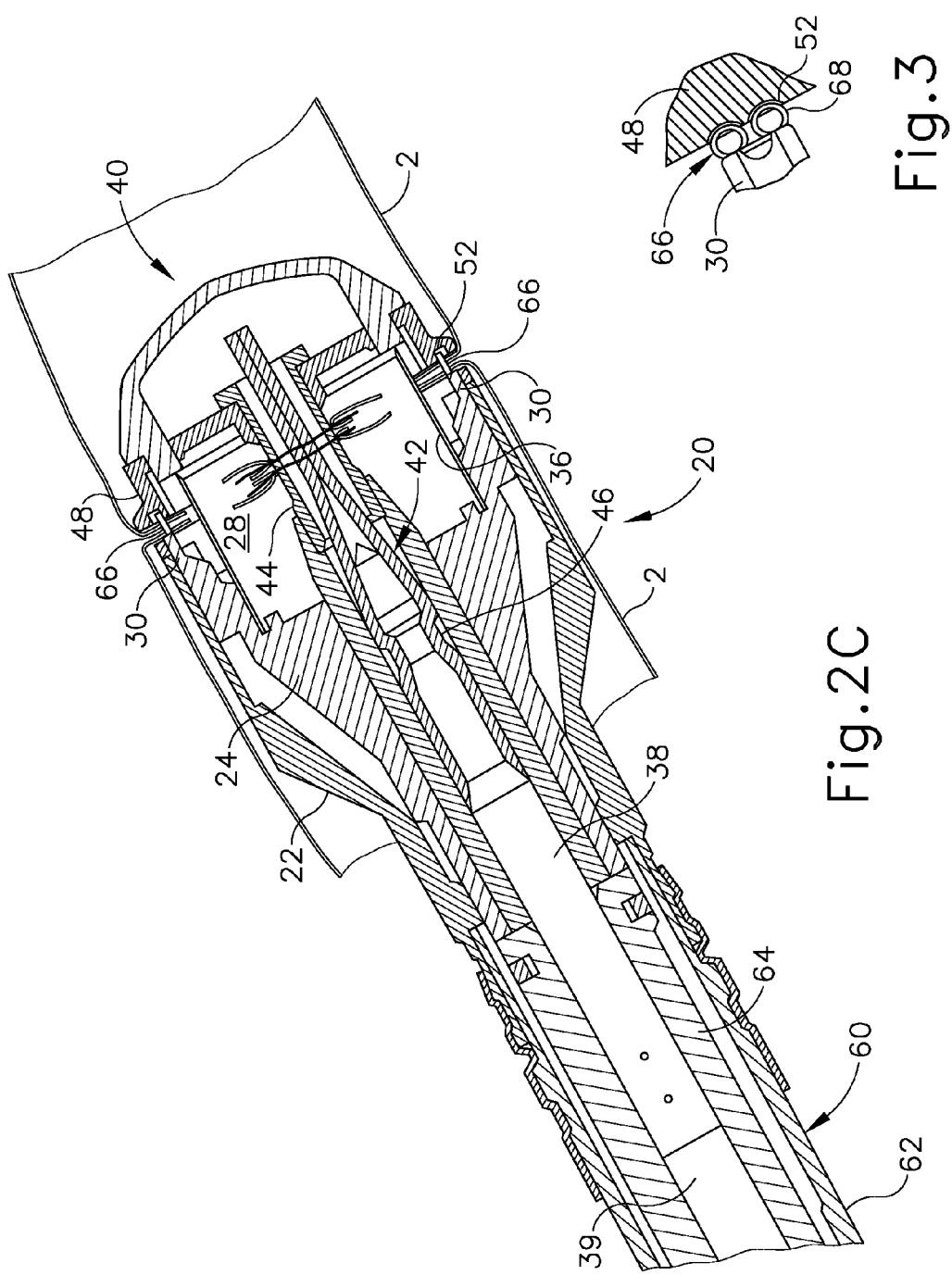

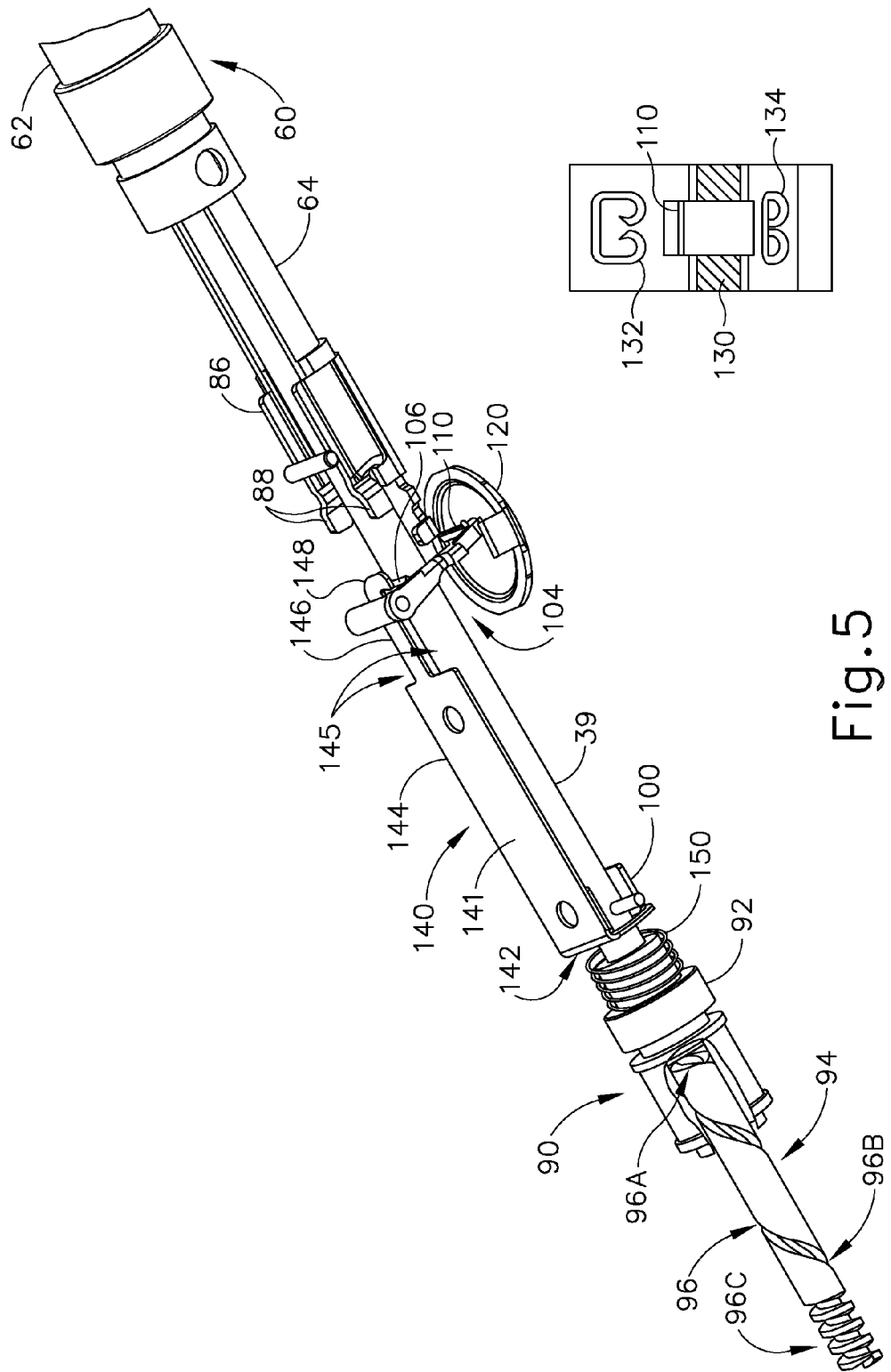

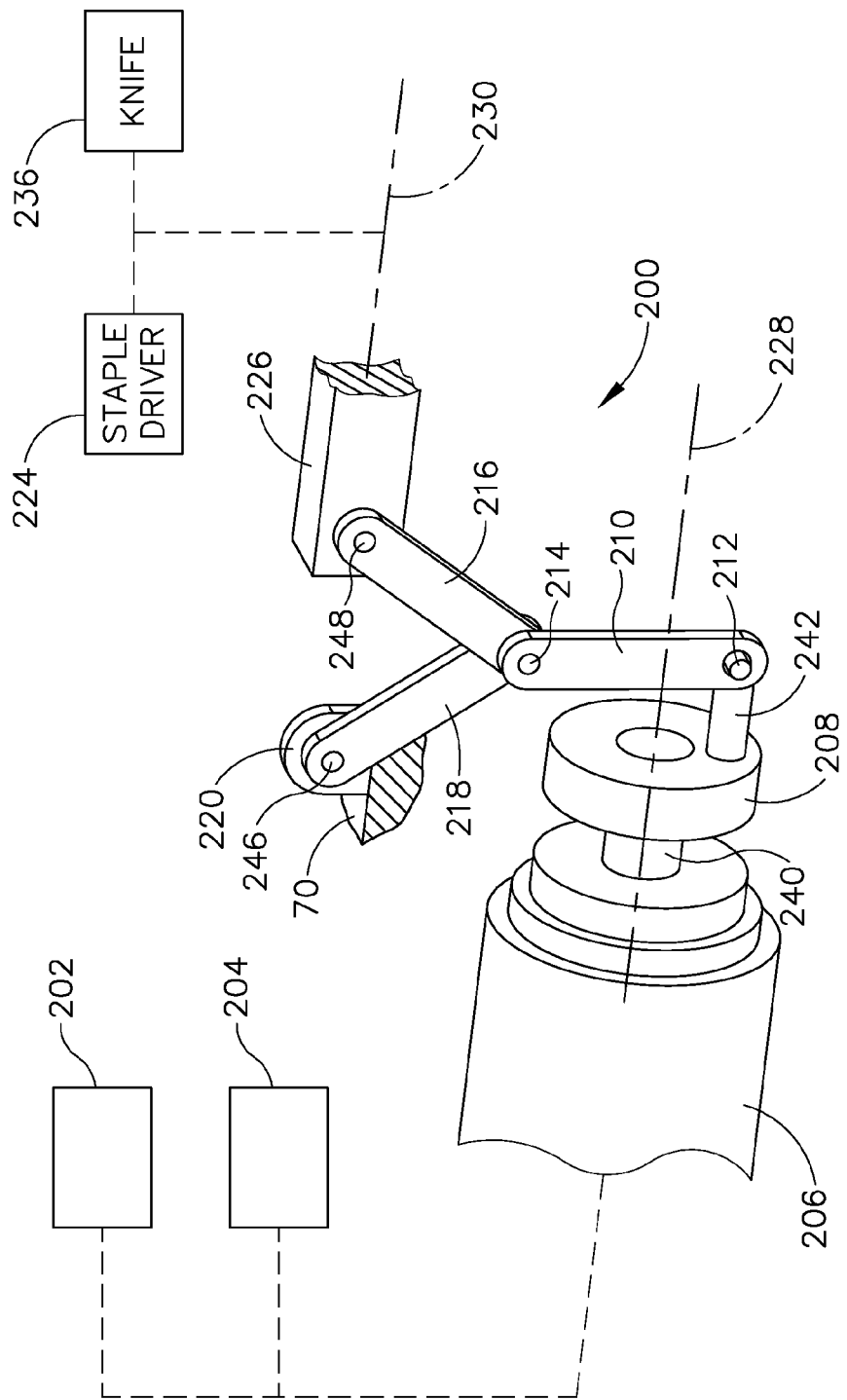

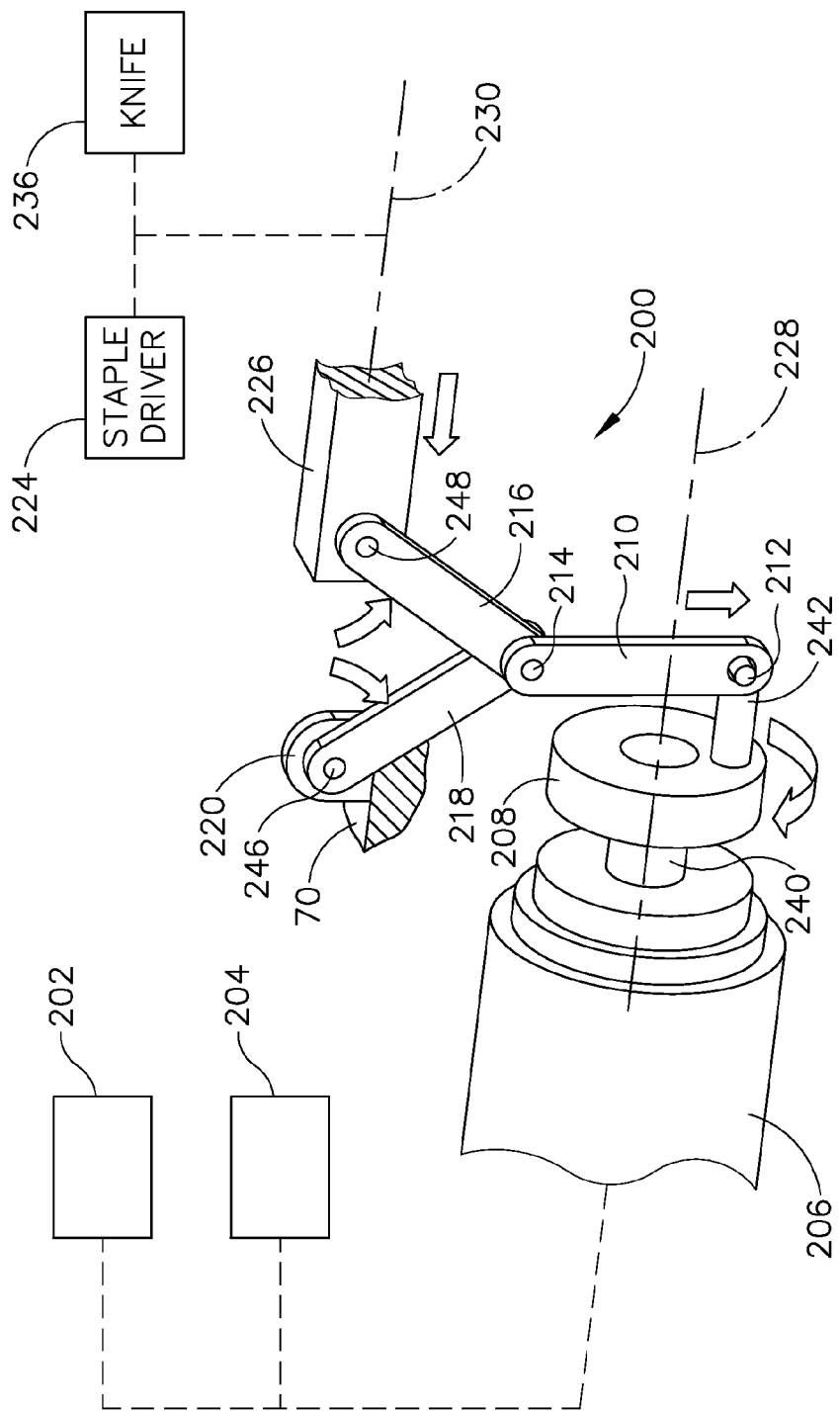

SURGICAL STAPLING INSTRUMENT WITH DRIVE ASSEMBLY HAVING TOGGLE FEATURES

BACKGROUND

In some settings, a surgeon may want to position a surgical instrument through an orifice of the patient and use the instrument to adjust, position, attach, and/or otherwise interact with tissue within the patient. For instance, in some surgical procedures (e.g., colorectal, bariatric, thoracic, etc.), portions of the gastrointestinal tract and/or esophagus, etc. may be cut and removed to eliminate undesirable tissue or for other reasons. Once the desired tissue is removed, the remaining portions may need to be recoupled together in an end-to-end anastomosis. One such tool for accomplishing these anastomotic procedures is a circular stapler that is inserted through a patient's naturally occurring orifice. Some circular staplers are configured to sever tissue and staple tissue substantially simultaneously. For instance, a circular stapler may sever excess tissue that is interior to an annular array of staples at an anastomosis, to provide a substantially smooth transition between lumen sections that are joined at the anastomosis.

Examples of circular surgical staplers are described in U.S. Pat. No. 5,205,459, entitled "Surgical Anastomosis Stapling Instrument," issued Apr. 27, 1993; U.S. Pat. No. 5,271,544, entitled "Surgical Anastomosis Stapling Instrument," issued Dec. 21, 1993; U.S. Pat. No. 5,275,322, entitled "Surgical Anastomosis Stapling Instrument," issued Jan. 4, 1994; U.S. Pat. No. 5,285,945, entitled "Surgical Anastomosis Stapling Instrument," issued Feb. 15, 1994; U.S. Pat. No. 5,292,053, entitled "Surgical Anastomosis Stapling Instrument," issued Mar. 8, 1994; U.S. Pat. No. 5,333,773, entitled "Surgical Anastomosis Stapling Instrument," issued Aug. 2, 1994; U.S. Pat. No. 5,350,104, entitled "Surgical Anastomosis Stapling Instrument," issued Sep. 27, 1994; and U.S. Pat. No. 5,533,661, entitled "Surgical Anastomosis Stapling Instrument," issued Jul. 9, 1996; and U.S. Pub. No. 2012/0292372, entitled "Low Cost Anvil Assembly for a Circular Stapler," now U.S. Pat. No. 8,910,847, issued on Dec. 16, 2014, published Nov. 22, 2012. The disclosure of each of the above-cited U.S. patents and U.S. patent application Publication is incorporated by reference herein. Some such staplers are operable to clamp down on layers of tissue, cut through the clamped layers of tissue, and drive staples through the layers of tissue to substantially seal the severed layers of tissue together near the severed ends of the tissue layers, thereby joining two severed ends of an anatomical lumen.

Merely additional other exemplary surgical staplers are disclosed in U.S. Pat. No. 4,805,823, entitled "Pocket Configuration for Internal Organ Staplers," issued Feb. 21, 1989; U.S. Pat. No. 5,415,334, entitled "Surgical Stapler and Staple Cartridge," issued May 16, 1995; U.S. Pat. No. 5,465,895, entitled "Surgical Stapler Instrument," issued Nov. 14, 1995; U.S. Pat. No. 5,597,107, entitled "Surgical Stapler Instrument," issued Jan. 28, 1997; U.S. Pat. No. 5,632,432, entitled "Surgical Instrument," issued May 27, 1997; U.S. Pat. No. 5,673,840, entitled "Surgical Instrument," issued Oct. 7, 1997; U.S. Pat. No. 5,704,534, entitled "Articulation Assembly for Surgical Instruments," issued Jan. 6, 1998; U.S. Pat. No. 5,814,055, entitled "Surgical Clamping Mechanism," issued Sep. 29, 1998; U.S. Pat. No. 6,978,921, entitled "Surgical Stapling Instrument Incorporating an E-Beam Firing Mechanism," issued Dec. 27, 2005; U.S. Pat. No. 7,000,818, entitled "Surgical Stapling Instrument Having Separate Distinct Closing and Firing Systems," issued Feb. 21, 2006; U.S. Pat. No. 7,143,923, entitled "Surgical Stapling Instrument Having a Firing Lockout for an Unclosed Anvil," issued Dec. 5, 2006; U.S. Pat. No. 7,303,108, entitled "Surgical Stapling Instrument Incorporating a Multi-Stroke Firing Mechanism with a Flexible Rack," issued Dec. 4, 2007; U.S. Pat. No. 7,367,485, entitled "Surgical Stapling Instrument Incorporating a Multistroke Firing Mechanism Having a Rotary Transmission," issued May 6, 2008; U.S. Pat. No. 7,380,695, entitled "Surgical Stapling Instrument Having a Single Lockout Mechanism for Prevention of Firing," issued Jun. 3, 2008; U.S. Pat. No. 7,380,696, entitled "Articulating Surgical Stapling Instrument Incorporating a Two-Piece E-Beam Firing Mechanism," issued Jun. 3, 2008; U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; and U.S. Pat. No. 7,721,930, entitled "Disposable Cartridge with Adhesive for Use with a Stapling Device," issued May 25, 2010. The disclosure of each of the above-cited U.S. Patents is incorporated by reference herein. While the surgical staplers referred to above are described as being used in endoscopic procedures, it should be understood that such surgical staplers may also be used in open procedures and/or other non-endoscopic procedures.

While various kinds of surgical stapling instruments and associated components have been made and used, it is believed that no one prior to the inventor(s) has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 2C depicts an enlarged longitudinal cross-sectional view of the stapling head assembly of FIG. 2A showing an exemplary staple driver and blade in a fired position;

FIG. 3 depicts an enlarged partial cross-sectional view of an exemplary staple formed against the anvil;

FIG. 5 depicts an enlarged partial perspective view of an exemplary indicator assembly of the surgical instrument of FIG. 1 showing an indicator window and indicator lever;

FIG. 6 depicts an diagrammatic view of the indicator window of FIG. 5 showing an exemplary indicator bar and exemplary corresponding staple representations;

FIG. 7A depicts a side, perspective view of an exemplary alternative drive assembly for use with the circular stapling surgical instrument of FIG. 1 in a pre-firing position;

FIG. 7C depicts a side, perspective view of the drive assembly of FIG. 7A, in a post-firing position with a vertical link descended;

Figure 1:
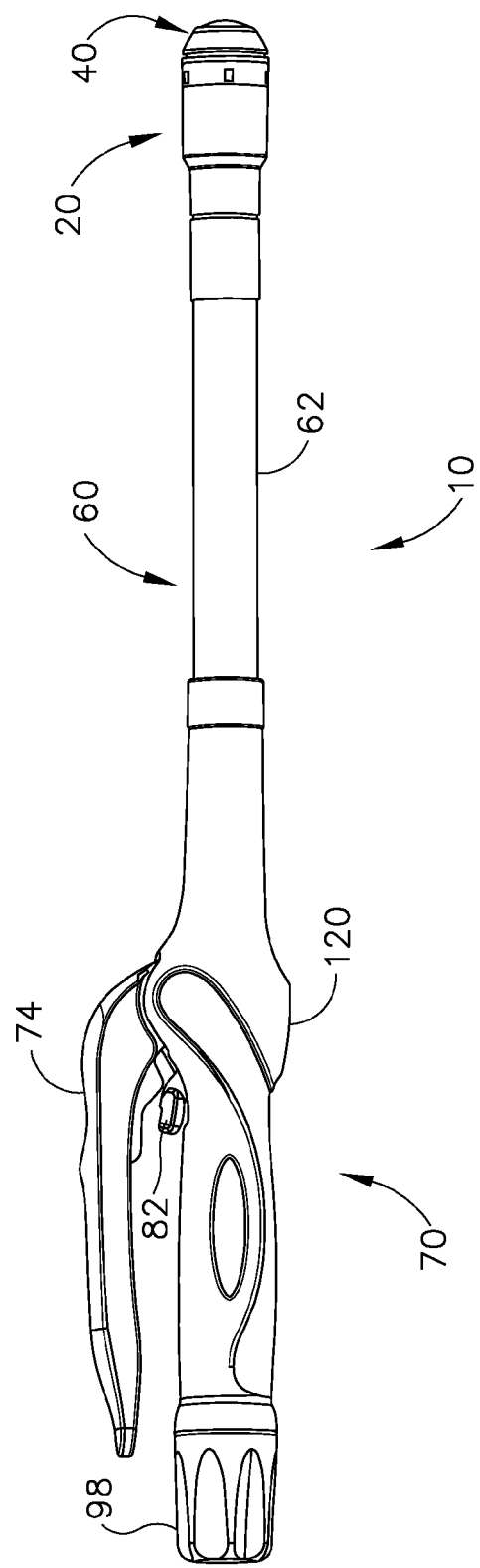
FIG. 1 depicts a side elevation view of an exemplary circular stapling surgical instrument.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

I. Overview of Exemplary Circular Stapling Surgical Instrument

FIGS. 1-6 depict an exemplary circular surgical stapling instrument (10) having a stapling head assembly (20), a shaft assembly (60), and an actuator handle assembly (70), each of which will be described in more detail below. Shaft assembly (60) extends distally from actuator handle assembly (70) and stapling head assembly (20) is coupled to a distal end of shaft assembly (60). In brief, actuator handle assembly (70) is operable to actuate a staple driver (24) of stapling head assembly (20) to drive a plurality of staples (66) out of stapling head assembly (20). Staples (66) are bent to form completed staples by an anvil (40) that is attached at the distal end of instrument (10). Accordingly, tissue (2), shown in FIGS. 2A-2C, may be stapled utilizing instrument (10).

In the present example, instrument (10) comprises a closure system and a firing system. The closure system comprises a trocar (38), a trocar actuator (39), and a rotating knob (98). An anvil (40) may be coupled to a distal end of trocar (38). Rotating knob (98) is operable to longitudinally translate trocar (38) relative to stapling head assembly (20), thereby translating anvil (40) when anvil (40) is coupled to trocar (38), to clamp tissue between anvil (40) and stapling head assembly (20). The firing system comprises a trigger (74), a trigger actuation assembly (84), a driver actuator (64), and a staple driver (24). Staple driver (24) includes a knife (36) configured to sever tissue when staple driver (24) is actuated longitudinally. In addition, staples (66) are positioned distal to a plurality of staple driving features (30) of staple driver (24) such that staple driver (24) also drives staples (66) distally when staple driver (24) is actuated longitudinally. Thus, when trigger (74) is actuated and trigger actuation assembly (84) actuates staple driver (24) via driver actuator (64), knife (36) and members (30) substantially simultaneously sever tissue (2) and drive staples (66) distally relative to stapling head assembly (20) into tissue. The components and functionalities of the closure system and firing system will now be described in greater detail.

A. Exemplary Anvil

Figure 2A:
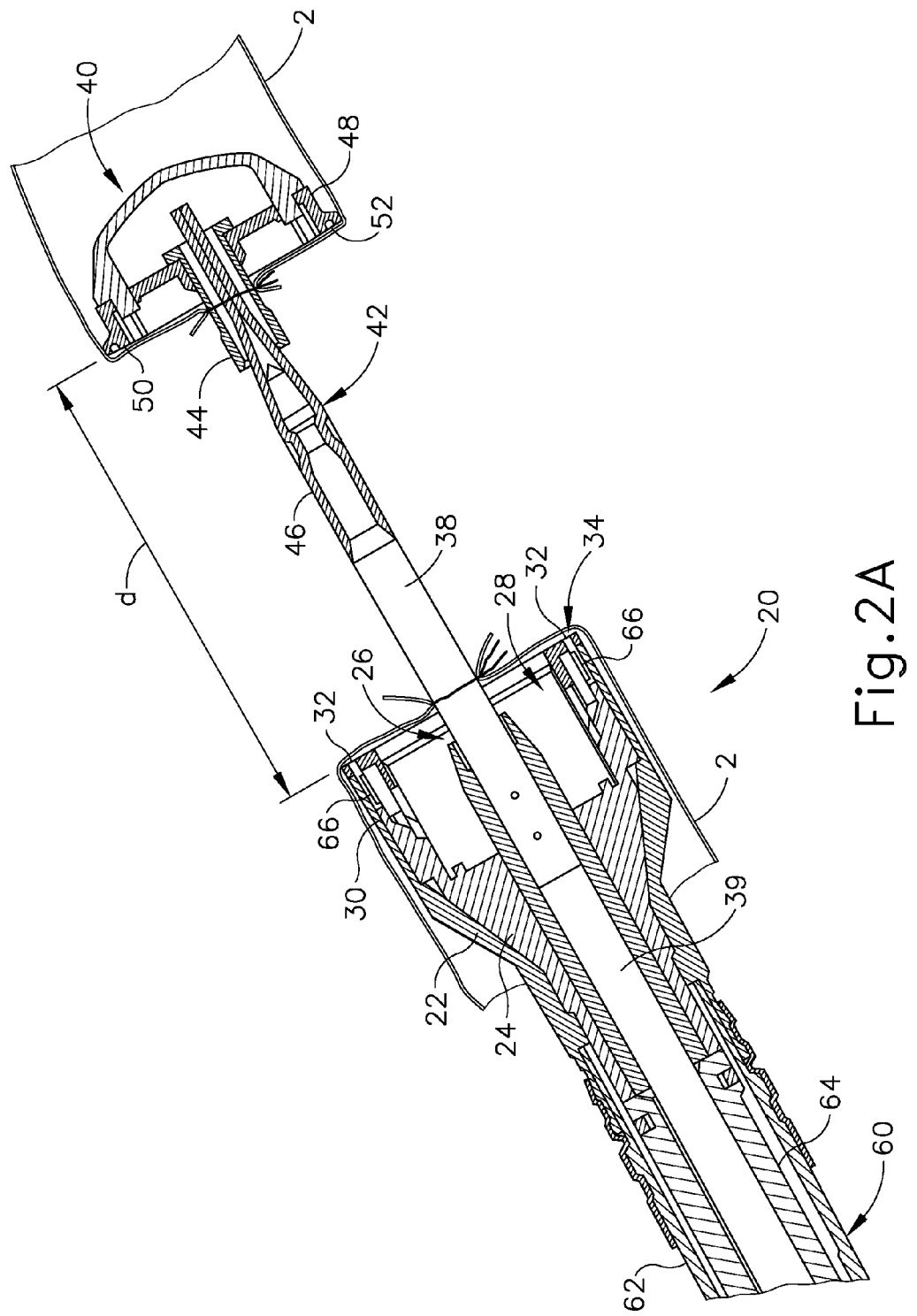
FIG. 2A depicts an enlarged longitudinal cross-section view of an exemplary stapling head assembly of the instrument of FIG. 1 showing an exemplary anvil in an open position.
Figure 2B:
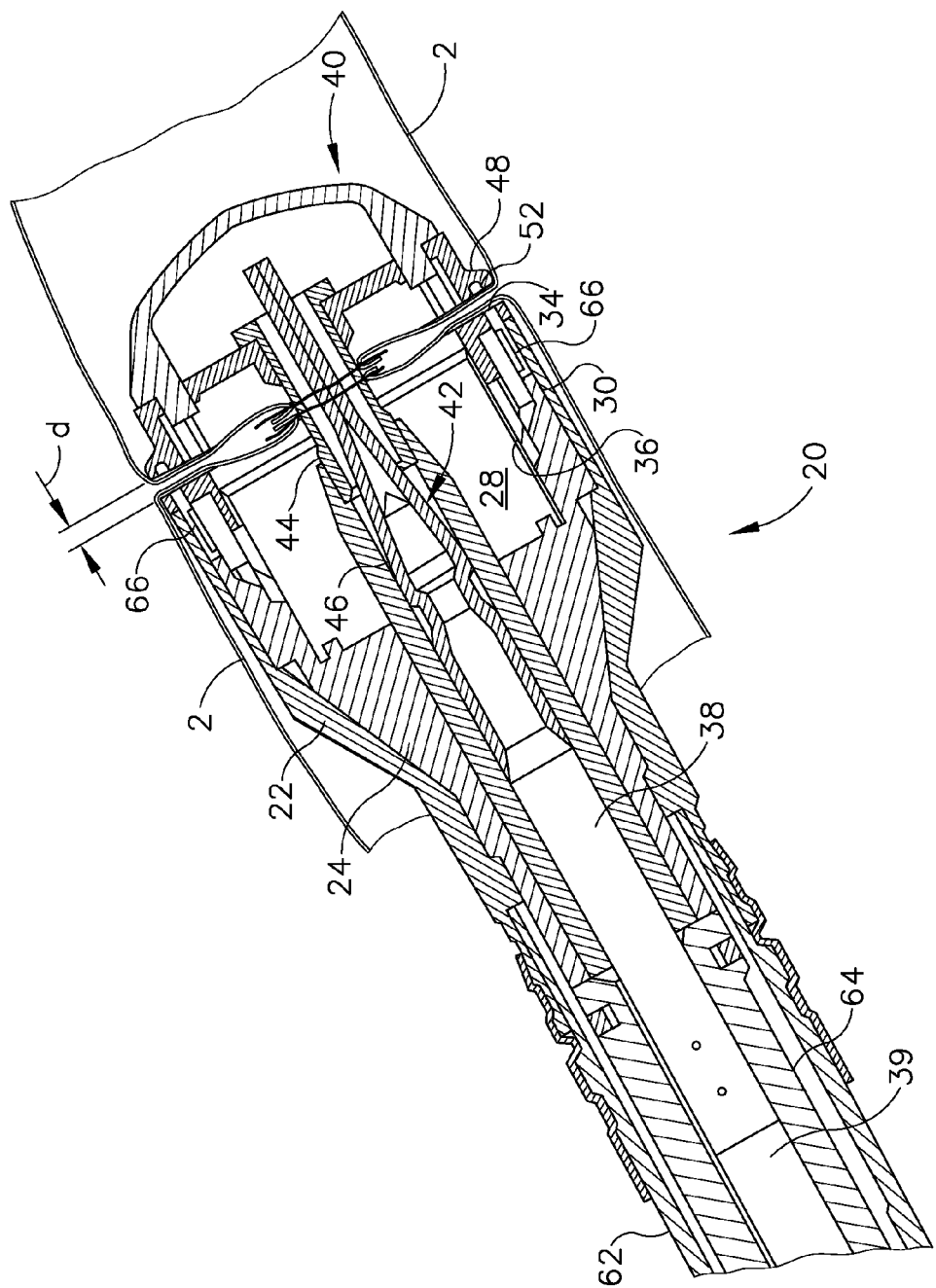
FIG. 2B depicts an enlarged longitudinal cross-sectional view of the stapling head assembly of FIG. 2A showing the anvil in a closed position.

As shown in FIGS. 1-2C, anvil (40) is selectively coupleable to instrument (10) to provide a surface against which staples (66) may be bent to staple material contained between stapling head assembly (20) and anvil (40). Anvil (40) of the present example is selectively coupleable to a trocar or pointed rod (38) that extends distally relative to stapling head assembly (20). Referring to FIGS. 2A-2C, anvil (40) is selectively coupleable via the coupling of a proximal shaft (42) of anvil (40) to a distal tip of trocar (38). Anvil (40) comprises a generally circular anvil head (48) and a proximal shaft (42) extending proximally from anvil head (48). In the example shown, proximal shaft (42) comprises a tubular member (44) having resiliently biased retaining clips (46) to selectively couple anvil (40) to trocar (38), though this is merely optional, and it should be understood that other retention features for coupling anvil (40) to trocar (38) may be used as well. For example, C-clips, clamps, threading, pins, adhesives, etc. may be employed to couple anvil (40) to trocar (38). In addition, while anvil (40) is described as selectively coupleable to trocar (38), in some versions proximal shaft (42) may include a one-way coupling feature such that anvil (40) cannot be removed from trocar (38) once anvil (40) is attached. Merely exemplary one-way features include barbs, one way snaps, collets, collars, tabs, bands, etc. Of course still other configurations for coupling anvil (40) to trocar (38) will be apparent to one of ordinary skill in the art in view of the teachings herein. For instance, trocar (38) may instead be a hollow shaft and proximal shaft (42) may comprise a sharpened rod that is insertable into the hollow shaft.

Anvil head (48) of the present example comprises a plurality of staple forming pockets (52) formed in a proximal face (50) of anvil head (48). Accordingly, when anvil (40) is in the closed position and staples (66) are driven out of stapling head assembly (20) into staple forming pockets (52), as shown in FIG. 2C, legs (68) of staples (66) are bent to form completed staples.

With anvil (40) as a separate component, it should be understood that anvil (40) may be inserted and secured to a portion of tissue (2) prior to being coupled to stapling head assembly (20). By way of example only, anvil (40) may be inserted into and secured to a first tubular portion of tissue (2) while instrument (10) is inserted into and secured to a second tubular portion of tissue (2). For instance, the first tubular portion of tissue (2) may be sutured to or about a portion of anvil (40), and the second tubular portion of tissue (2) may be sutured to or about trocar (38).

As shown in FIG. 2A, anvil (40) is then coupled to trocar (38). Trocar (38) of the present example is shown in a distal most actuated position. Such an extended position for trocar (38) may provide a larger area to which tissue (2) may be coupled prior to attachment of anvil (40). In addition, the extended position of trocar (38) may also provide for easier attachment of anvil (40) to trocar (38). Trocar (38) further includes a tapered distal tip. Such a tip may be capable of piercing through tissue and/or aiding the insertion of anvil (40) on to trocar (38), though the tapered distal tip is merely optional. For instance, in other versions trocar (38) may have a blunt tip. In addition, or in the alternative, trocar (38) may include a magnetic portion (not shown) which may attract anvil (40) towards trocar (38). Of course still further configurations and arrangements for anvil (40) and trocar (38) will be apparent to one of ordinary skill in the art in view of the teachings herein.

When anvil (40) is coupled to trocar (38), the distance between a proximal face of the anvil (40) and a distal face of stapling head assembly (20) defines a gap distance d. Trocar (38) of the present example is translatable longitudinally relative to stapling head assembly (20) via an adjustment knob (98) located at a proximal end of actuator handle assembly (70), as will be described in greater detail below. Accordingly, when anvil (40) is coupled to trocar (38), rotation of adjustment knob (98) enlarges or reduces gap distance d by actuating anvil (40) relative to stapling head assembly (20). For instance, as shown sequentially in FIGS. 2A-2B, anvil (40) is shown actuating proximally relative to actuator handle assembly (70) from an initial, open position to a closed position, thereby reducing the gap distance d and the distance between the two portions of tissue (2) to be joined. Once the gap distance d is brought within a predetermined range, stapling head assembly (20) may be fired, as shown in FIG. 2C, to staple and sever tissue (2) between anvil (40) and stapling head assembly (20). Stapling head assembly (20) is operable to staple and sever tissue (2) by a user pivoting a trigger (74) of actuator handle assembly (70), as will be described in greater detail below.

As noted above, gap distance d corresponds to the distance between anvil (40) and stapling head assembly (20). When instrument (10) is inserted into a patient, this gap distance d may not be easily viewable. Accordingly, a moveable indicator bar (110), shown in FIGS. 5-6, is provided to be visible through an indicator window (120) positioned opposite to trigger (74). Indicator bar (110) is operable to move in response to rotation of adjustment knob (98) such that the position of indicator bar (110) is representative of the gap distance d. As shown in FIG. 6, indicator window (120) further comprises a scale (130) which indicates that the anvil gap is within a desired operating range (e.g., a green colored region or "green zone") and a corresponding staple compression representation at each end of scale (130). By way of example only, as shown in FIG. 6, a first staple image (132) depicts a large staple height while a second staple image (134) depicts a small staple height. Accordingly, a user can view the position of the coupled anvil (40) relative to the stapling head assembly (20) via indicator bar (110) and scale (130). The user may then adjust the positioning of anvil (40) via adjustment knob (98) accordingly.

Referring back to FIGS. 2A-2C, a user sutures a portion of tissue (2) about tubular member (44) such that anvil head (48) is located within a portion of the tissue (2) to be stapled. When tissue (2) is attached to anvil (40), retaining clips (46) and a portion of tubular member (44) protrude out from tissue (2) such that the user may couple anvil (40) to trocar (38). With tissue (2) coupled to trocar (38) and/or another portion of stapling head assembly (20), the user attaches anvil (40) to trocar (38) and actuates anvil (40) proximally towards stapling head assembly (20) to reduce the gap distance d. Once instrument (10) is within the operating range, the user then staples together the ends of tissue (2), thereby forming a substantially contiguous tubular portion of tissue (2).

Anvil (40) may be further constructed in accordance with at least some of the teachings of U.S. Pat. No. 5,205,459; U.S. Pat. No. 5,271,544; U.S. Pat. No. 5,275,322; U.S. Pat. No. 5,285,945; U.S. Pat. No. 5,292,053; U.S. Pat. No. 5,333,773; U.S. Pat. No. 5,350,104; U.S. Pat. No. 5,533,661; and/or U.S. Pub. No. 2012/0292372, now U.S. Pat. No. 8,910,847, issued on Dec. 16, 2014, the disclosures of which are incorporated by reference herein; and/or in accordance with other configurations as will be apparent to one of ordinary skill in the art in view of the teachings herein.

B. Exemplary Stapling Head Assembly

Stapling head assembly (20) of the present example is coupled to a distal end of shaft assembly (60) and comprises a tubular casing (22) housing a slidable staple driver (24) and a plurality of staples (66) contained within staple pockets (32). Staples (66) and staple pockets (32) are disposed in a circular array about tubular casing (22). In the present example, staples (66) and staple pockets (32) are disposed in a pair of concentric annular rows of staples (66) and staple pockets (32). Staple driver (24) is operable to actuate longitudinally within tubular casing (22) in response to rotation of trigger (74) of actuator handle assembly (70). As shown in FIGS. 2A-2C, staple driver (24) comprises a flared cylindrical member having a trocar opening (26), a central recess (28), and a plurality of members (30) disposed circumferentially about central recess (28) and extending distally relative to shaft assembly (60). Each member (30) is configured to contact and engage a corresponding staple (66) of the plurality of staples (66) within staple pockets (32). Accordingly, when staple driver (24) is actuated distally relative to actuator handle assembly (70), each member (30) drives a corresponding staple (66) out of its staple pocket (32) through a staple aperture (34) formed in a distal end of tubular casing (22). Because each member (30) extends from staple driver (24), the plurality of staples (66) are driven out of stapling head assembly (20) at substantially the same time. When anvil (40) is in the closed position, staples (66) are driven into staple forming pockets (52) to bend legs (68) of the staples (66), thereby stapling the material located between anvil (40) and stapling head assembly (20). FIG. 3 depicts one merely exemplary staple (66) driven by a member (30) into a staple forming pocket (32) of anvil (40) to bend legs (68).

Staple driver (24) further includes a cylindrical knife (36) that is coaxial to trocar opening (26) and inset from staple pockets (32). In the present example, cylindrical knife (36) is disposed within central recess (28) to translate distally with staple driver (24). When anvil (40) is secured to trocar (38), as described above, anvil head (48) provides a surface against which cylindrical knife (36) cuts the material contained between anvil (40) and stapling head assembly (20).

In some versions, anvil head (48) may include a recess (not shown) for cylindrical knife (36) to aid in cutting the material (e.g., by providing a cooperative shearing edge). In addition, or in the alternative, anvil head (48) may include one or more opposing cylindrical knives (not shown) offset from cylindrical knife (36) such that a scissor-type cutting action may be provided. Still other configurations will be apparent to one of ordinary skill in the art in view of the teachings herein. Stapling head assembly (20) is thus operable to both staple and cut tissue (2) substantially simultaneously in response to actuation by actuator handle assembly (70).

Of course stapling head assembly (20) may be further constructed in accordance with at least some of the teachings of U.S. Pat. No. 5,205,459; U.S. Pat. No. 5,271,544; U.S. Pat. No. 5,275,322; U.S. Pat. No. 5,285,945; U.S. Pat. No. 5,292,053; U.S. Pat. No. 5,333,773; U.S. Pat. No. 5,350,104; U.S. Pat. No. 5,533,661; and/or U.S. Pub. No. 2012/0292372, now U.S. Pat. No. 8,910,847, issued on Dec. 16, 2014, the disclosures of which are incorporated by reference herein; and/or in accordance with other configurations as will be apparent to one of ordinary skill in the art in view of the teachings herein.

As noted previously, staple driver (24) includes a trocar opening (26). Trocar opening (26) is configured to permit trocar (38) to longitudinally slide relative to stapling head assembly (20) and/or shaft assembly (60). As shown in FIGS. 2A-2C, trocar (38) is coupled to a trocar actuator (39) such that trocar (38) can be actuated longitudinally via rotation of rotating knob (98), as will be described in greater detail below in reference to actuator handle assembly (70). In the present example, trocar actuator (39) comprises an elongated, relatively stiff shaft coupled to trocar (38), though this is merely optional. In some versions, actuator (39) may comprise a longitudinally stiff material while permitting lateral bending such that portions of instrument (10) may be selectively bent or curved during use; or instrument (10) may include a preset bent shaft assembly (60). One merely exemplary material is nitinol. When anvil (40) is coupled to trocar (38), trocar (38) and anvil (40) are translatable via actuator (39) to adjust the gap distance d between anvil (40) and stapling head assembly (20). Still further configurations for actuator (39) to longitudinally actuate trocar (38) will be apparent to one of ordinary skill in the art in view of the teachings herein.

C. Exemplary Shaft Assembly

Stapling head assembly (20) and trocar (38) are positioned at a distal end of shaft assembly (60), as shown in FIGS. 2A-2C. Shaft assembly (60) of the present example comprises an outer tubular member (62) and a driver actuator (64). Outer tubular member (62) is coupled to tubular casing (22) of stapling head assembly (20) and to a body (72) of actuator handle assembly (70), thereby providing a mechanical ground for the actuating components therein. The proximal end of driver actuator (64) is coupled to a trigger actuation assembly (84) of actuator handle assembly (70), described below. The distal end of driver actuator (64) is coupled to staple driver (24) such that the rotation of trigger (74) longitudinally actuates staple driver (24). As shown in FIGS. 2A-2C, driver actuator (64) comprises a tubular member having an open longitudinal axis such that actuator (39) coupled to trocar (38) may actuate longitudinally within and relative to driver actuator (64). Of course it should be understood that other components may be disposed within driver actuator (64) as will be apparent to one of ordinary skill in the art in view of the teachings herein.

Shaft assembly (60) may be further constructed in accordance with at least some of the teachings of U.S. Pat. No. 5,205,459; U.S. Pat. No. 5,271,544; U.S. Pat. No. 5,275,322; U.S. Pat. No. 5,285,945; U.S. Pat. No. 5,292,053; U.S. Pat. No. 5,333,773; U.S. Pat. No. 5,350,104; U.S. Pat. No. 5,533,661; and/or U.S. Pub. No. 2012/0292372, now U.S. Pat. No. 8,910,847, issued on Dec. 16, 2014, the disclosures of which are incorporated by reference herein; and/or in accordance with other configurations as will be apparent to one of ordinary skill in the art in view of the teachings herein.

D. Exemplary Actuator Handle Assembly

Figure 4A:
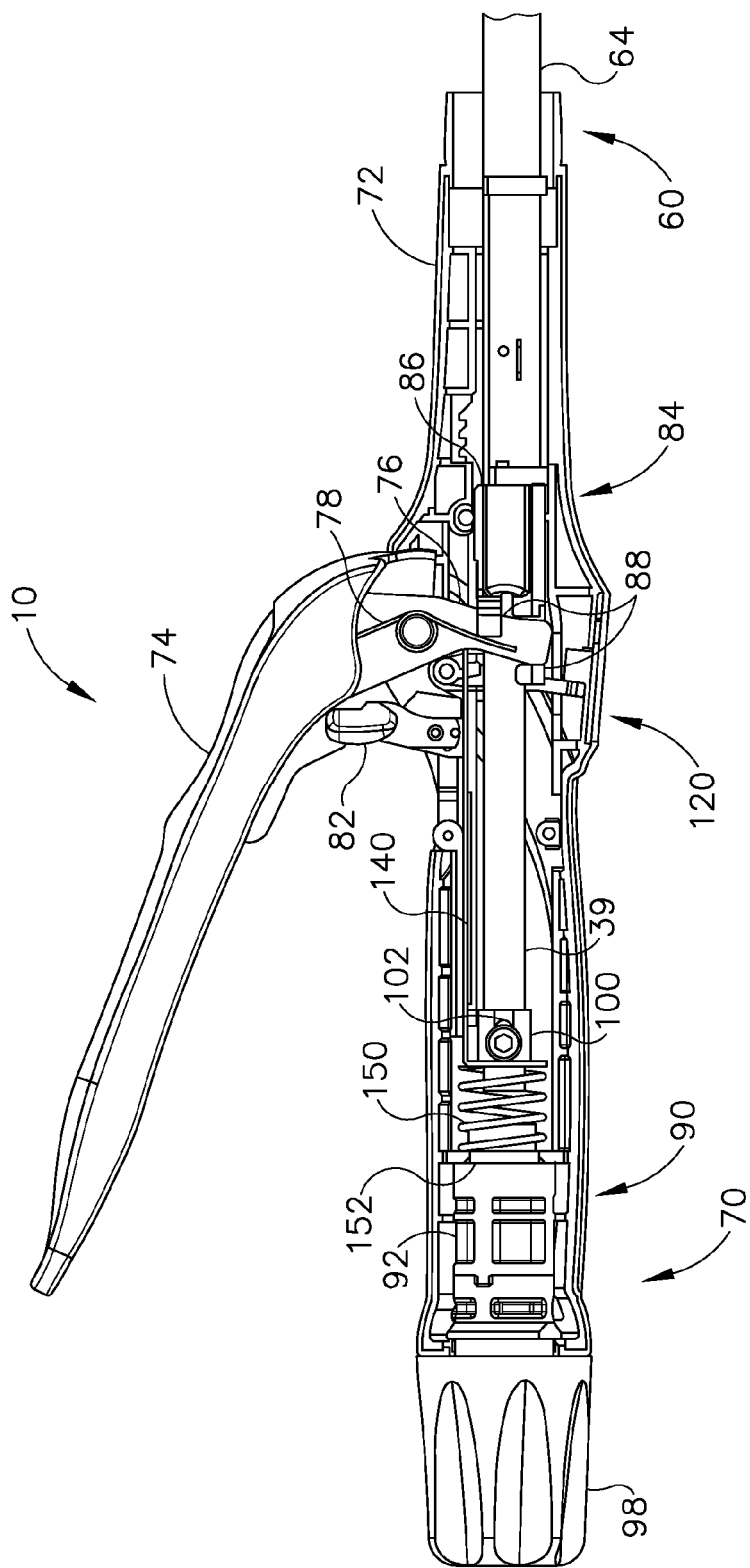
FIG. 4A depicts an enlarged side elevation view of an exemplary actuator handle assembly of the surgical instrument of FIG. 1 with a portion of the body removed, showing a trigger in an unfired position and a lockout feature in a locked position.
Figure 4B:
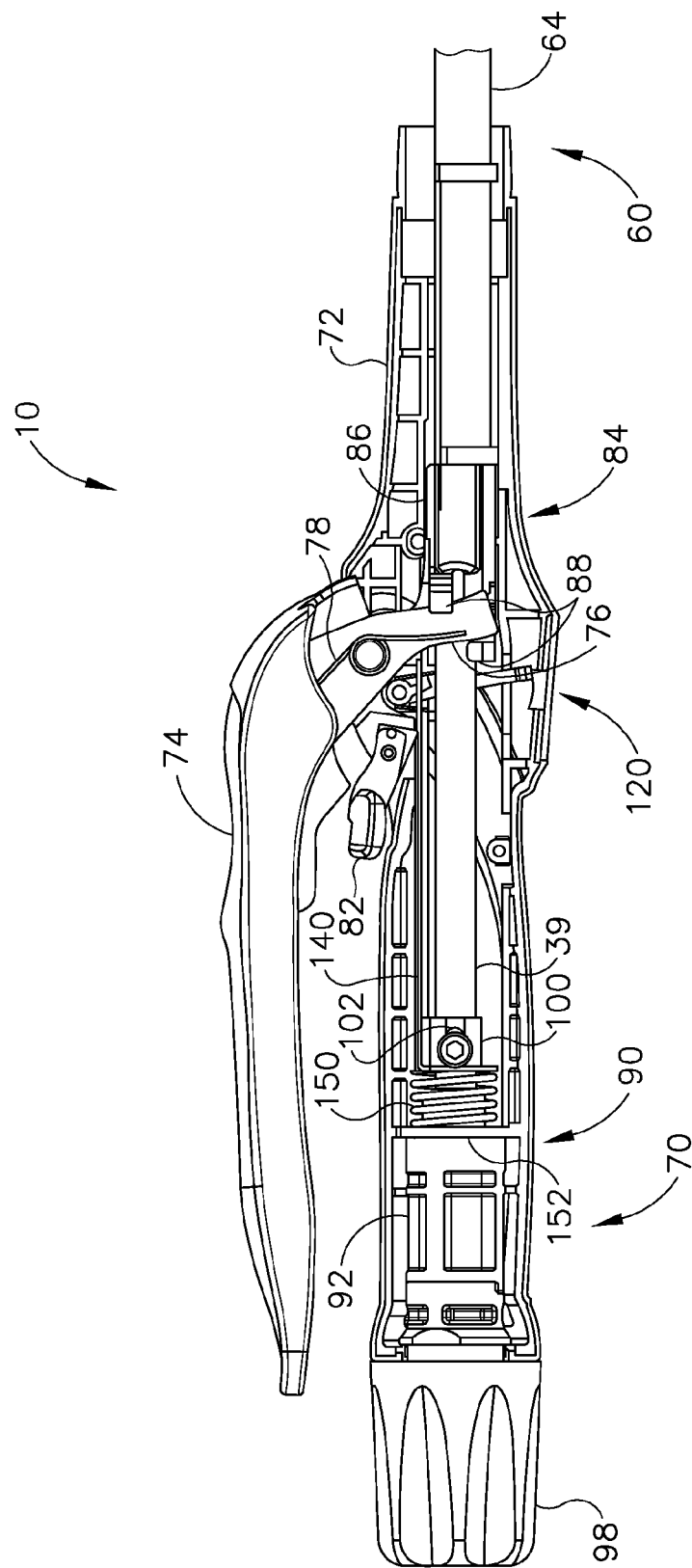
FIG. 4B depicts an enlarged side elevation view of the actuator handle assembly of FIG. 4A, showing the trigger in a fired position and the lockout feature in an unlocked position.

Referring now to FIGS. 4A-5, actuator handle assembly (70) comprises a body (72), a trigger (74), a lockout feature (82), a trigger actuation assembly (84), and a trocar actuation assembly (90). Trigger (74) of the present example is pivotably mounted to body (72) and is coupled to trigger actuation assembly (84) such that rotation of trigger (74) from an unfired position (shown in FIG. 4A) to a fired position (shown in FIG. 4B) actuates driver actuator (64) described above. A spring (78) is coupled to body (72) and trigger (74) to bias trigger (74) towards the unfired position. Lockout feature (82) is a pivotable member that is coupled to body (72). In a first, locked position, lockout feature (82) is pivoted upwards and away from body (72) such that lockout feature (82) engages trigger (74) and mechanically resists actuation of trigger (74) by a user. In a second, unlocked position, such as that shown in FIGS. 1 and 4B, lockout feature (82) is pivoted downward such that trigger (74) may be actuated by the user. Accordingly, with lockout feature (82) in the second position, trigger (74) can engage a trigger actuation assembly (84) to fire instrument (10).

As shown in FIGS. 4A-4B, trigger actuation assembly (84) of the present example comprises a slidable trigger carriage (86) engaged with a proximal end of driver actuator (64). Carriage (86) includes a set of tabs (88) on a proximal end of carriage (86) to retain and engage a pair of trigger arms (76) extending from trigger (74). Accordingly, when trigger (74) is pivoted, carriage (86) is actuated longitudinally and transfers the longitudinal motion to driver actuator (64). In the example shown, carriage (86) is fixedly coupled to the proximal end of driver actuator (64), though this is merely optional. Indeed, in one merely exemplary alternative, carriage (86) may simply abut driver actuator (64) while a distal spring (not shown) biases driver actuator (64) proximally relative to actuator handle assembly (70).

Trigger actuation assembly (84) may be further constructed in accordance with at least some of the teachings of U.S. Pat. No. 5,205,459; U.S. Pat. No. 5,271,544; U.S. Pat. No. 5,275,322; U.S. Pat. No. 5,285,945; U.S. Pat. No. 5,292,053; U.S. Pat. No. 5,333,773; U.S. Pat. No. 5,350,104; U.S. Pat. No. 5,533,661; and/or U.S. Pub. No. 2012/0292372, now U.S. Pat. No. 8,910,847, issued on Dec. 16, 2014, the disclosures of which are incorporated by reference herein; and/or in accordance with other configurations as will be apparent to one of ordinary skill in the art in view of the teachings herein.

Body (72) also houses a trocar actuation assembly (90) configured to actuate trocar (38) longitudinally in response to rotation of adjustment knob (98). As best shown in FIGS. 4A-5, trocar actuation assembly (90) of the present example comprises adjustment knob (98), a grooved shank (94), and a sleeve (92). Grooved shank (94) of the present example is located at a proximal end of trocar actuator (39), though it should be understood that grooved shank (94) and trocar actuator (39) may alternatively be separate components that engage to transmit longitudinal movement. While grooved shank (94) is configured to translate within body (72), grooved shank (94) does not rotate within body (72). Adjustment knob (98) is rotatably supported by the proximal end of body (72) and is operable to rotate sleeve (92), which is engaged with grooved shank (94) via an internal tab (not shown). Adjustment knob (98) also defines internal threading (not shown) as will be described in greater detail below. Grooved shank (94) of the present example comprises a continuous groove (96) formed in the outer surface of grooved shank (94). Accordingly, when adjustment knob (98) is rotated, the internal tab of sleeve (92) rides within groove (96) and grooved shank (94) is longitudinally actuated relative to sleeve (92). Since grooved shank (94) is located at the proximal end of trocar actuator (39), rotating adjustment knob (98) in a first direction advances trocar actuator (39) distally relative to actuator handle assembly (70). Accordingly, the gap distance d between anvil (40) and stapling head assembly (20) is increased. By rotating adjustment knob (98) in the opposite direction, trocar actuator (39) is actuated proximally relative to actuator handle assembly (70) to reduce the gap distance d between anvil (40) and stapling head assembly (20). Thus, trocar actuation assembly (90) is operable to actuate trocar (38) in response to rotating adjustment knob (98). Of course other configurations for trocar actuation assembly (90) will be apparent to one of ordinary skill in the art in view of the teachings herein.

Groove (96) of the present example comprises a plurality of different portions (96A, 96B, 96C) that have a varying pitch or number of grooves per axial distance. The present groove (96) is divided into a distal portion (96A), a middle portion (96B) and a proximal portion (96C). As shown in FIG. 5, distal portion (96A) comprises a fine pitch or a high number of grooves over a short axial length of grooved shank (94). Middle portion (96B) comprises a section with comparably coarser pitch or fewer grooves per axial length such that relatively few rotations are required for the internal tab of sleeve (92) to traverse a long axial distance. When anvil (40) is in an initial, distal position in relation to stapling head assembly (20), the internal tab of sleeve (92) is positioned in middle portion (96B). Accordingly, the gap distance d may be quickly reduced through relatively few rotations of adjustment knob (98) while the internal tab of sleeve (92) traverses middle portion (96B). Proximal portion (96C) of the present example is substantially similar to distal portion (96A) and comprises a fine pitch or a high number of grooves over a short axial distance of grooved shank (94) such that a large number of rotations are required to traverse the short axial distance. Proximal portion (96C) of the present example is engaged by the internal threading defined by knob (98) when anvil (40) is substantially near to stapling head assembly (20), such that indicator bar (110) moves within indicator window (120) along scale (130) to indicate that the anvil gap is within a desired operating range, as will be described in more detail below. Accordingly, when grooved shank (94) reaches a proximal position where the proximal portion (96C) of groove (96) engages the internal threading of knob (98), each rotation of adjustment knob (98) may reduce the gap distance d by a relatively small amount to provide for fine tuning. It should be understood that the internal tab of sleeve (92) may be disengaged from groove (96) when proximal portion (96C) is engaged with the internal threading of knob (98).

Trocar actuation assembly (90) may be further constructed in accordance with at least some of the teachings of U.S. Pat. No. 5,205,459; U.S. Pat. No. 5,271,544; U.S. Pat. No. 5,275,322; U.S. Pat. No. 5,285,945; U.S. Pat. No. 5,292,053; U.S. Pat. No. 5,333,773; U.S. Pat. No. 5,350,104; U.S. Pat. No. 5,533,661, the disclosures of which are incorporated by reference herein; and/or in accordance with other configurations as will be apparent to one of ordinary skill in the art in view of the teachings herein.

In the example shown in FIGS. 4A-4B, a U-shaped clip (100) is attached to an intermediate portion of trocar actuator (39) located distally of grooved shank (94). In the present example, an extension of trocar actuator (39) engages a slot in the housing of handle assembly (70) to prevent trocar actuator (39) from rotating about its axis when adjustment knob (98) is rotated. U-shaped clip (100) of the present example further includes an elongated slot (102) on each of its opposite sides for receiving an attachment member, such as a screw, bolt, pin, etc., to selectively adjust the longitudinal position of elongated slot (102) of U-shaped clip (100) relative to trocar actuator (39) for purposes of calibrating indicator bar (110) relative to scale (130). In some versions, the attachment member (e.g., screw, bolt, pin, etc.) engages with a portion of body (72) to substantially prevent trocar actuator (39) from rotating about its axis when adjustment knob (98) is rotated.

As shown in FIG. 5, actuator handle assembly (70) further includes an indicator bracket (140) configured to engage and pivot an indicator (104). Indicator bracket (140) of the present example is slidable relative to body (72) along a pair of slots formed on body (72). Indicator bracket (140) comprises a rectangular plate (144), an indicator arm (146), and an angled flange (142). Angled flange (142) is formed at the proximal end of rectangular plate (144) and includes an aperture (not shown) to slidable mount onto trocar actuator (39) and/or grooved shank (94). A coil spring (150) is interposed between flange (142) and a boss (152) to bias flange (142) against U-shaped clip (100). Accordingly, when U-shaped clip (100) actuates distally with trocar actuator (39) and/or grooved shank (94), coil spring (150) urges indicator bracket (140) to travel distally with U-shaped clip (100). In addition, U-shaped clip (100) urges indicator bracket (140) proximally relative to boss (152) when trocar actuator (39) and/or grooved shank (94) translate proximally, thereby compressing coil spring (150). Of course, it should be understood that in some versions indicator bracket (140) may be fixedly attached to trocar actuator (39) and/or grooved shank (94).

In the present example, a portion of lockout feature (82) abuts a surface (141) of indicator bracket (140) when indicator bracket (140) is in a longitudinal position that does not correspond to when the anvil gap is within a desired operating range (e.g., a green colored region or "green zone"). When the anvil gap is within a desired operating range (e.g., a green colored region or "green zone"), indicator bracket (140) narrows to provide a pair of gaps (145) on either side of an indicator arm (146) that permits lockout feature (82) to pivot, thereby releasing trigger (74). Accordingly, lockout feature (82) and indicator bracket (140) can substantially prevent a user from releasing and operating trigger (74) until anvil (40) is in a predetermined operating range. Of course it should be understood that lockout feature (82) may be omitted entirely in some versions.

This operating range may be visually communicated to the user via an indicator bar (110) of an indicator (104) shown against a scale (130), described briefly above. At the distal end of indicator bracket (140) is a distally projecting indicator arm (146) which terminates at a laterally projecting finger (148) for controlling the movement of indicator (104). Indicator arm (146) and finger (148), best shown in FIG. 5, are configured to engage a tab (106) of indicator (104) such that indicator (104) is pivoted when indicator bracket (140) is actuated longitudinally. In the present example, indicator (104) is pivotably coupled to body (72) at a first end of indicator (104), though this is merely optional and other pivot points for indicator (104) will be apparent to one of ordinary skill in the art in view of the teachings herein. An indicator bar (110) is positioned on the second end of indicator (104) such that indicator bar (110) moves in response to the actuation of indicator bracket (140). Accordingly, as discussed above, indicator bar (110) is displayed through an indicator window (120) against a scale (130) (shown in FIG. 6) to show the relative gap distance d between anvil (40) and stapling head assembly (20).

Of course indicator bracket (140), indicator (104), and/or actuator handle assembly (70) may be further constructed in accordance with at least some of the teachings of U.S. Pat. No. 5,205,459; U.S. Pat. No. 5,271,544; U.S. Pat. No. 5,275,322; U.S. Pat. No. 5,285,945; U.S. Pat. No. 5,292,053; U.S. Pat. No. 5,333,773; U.S. Pat. No. 5,350,104; U.S. Pat. No. 5,533,661; and/or U.S. Pub. No. 2012/0292372, now U.S. Pat. No. 8,910,847, issued on Dec. 16, 2014, the disclosures of which are incorporated by reference herein; and/or in accordance with other configurations as will be apparent to one of ordinary skill in the art in view of the teachings herein.

II. Exemplary Motorized Actuator

In some instances, it may be desirable to drive staples (66) and knife (36) in a way that avoids manually driving circular surgical stapling instrument (10). For instance, in the event that the operator has inadequate hand strength to actuate circular surgical stapling instrument (10), it may be desirable to provide a motorized assembly for staple driver (24) and knife (36). Motorizing at least part of instrument (10) may also reduce the risk of operator error in driving staple driver (24) and knife (36). In some cases, operator error with a manually driven instrument (10) may result in instrument (10) failing to actuate fully. This may occur when an operator fails to fully manually actuate trigger (74), which may result in staples (66) not fully forming and thus not fully securing an anastomosis. Thus, motorizing the driving of staple driver (24) and knife (36) may ensure that knife (36) is fully driven to cut tissue, and that staples (66) are fully deployed to fasten tissue, in a single drive stroke.

However, it may not necessarily be desirable to motorize all portions of circular surgical stapling instrument (10). For instance, it may be desirable to maintain manual adjustment of knob (98) or a similar feature to control the distance d between anvil (40) and stapling head assembly (20). Other suitable portions of circular surgical stapling instrument (10) may also rely on manual actuation despite motorization of other features, as will be apparent to one of ordinary skill in the art in view of the teachings herein.

A. Exemplary Motorized Toggle Assembly

FIG. 7A shows an exemplary alternative drive assembly (200) that may be used or incorporated with circular surgical stapling instrument (10) to provide motorized driving of staples (66) and knife (36). In particular, drive assembly (200) of this example is in communication with a staple driver (224) and a knife (236) via shaft (226). Staple driver (224) and knife (236) are substantially similar to staple driver (24) and knife (36) described above and shown in FIG. 2B. Shaft (226) of drive assembly (200) is operable to drive staple driver (224) longitudinally; and is substantially similar to drive actuator (64) of circular surgical stapling instrument (10) described above and shown in FIG. 2A. In the present example, shaft (226) comprises a beam-like structure in communication with staple driver (224) and knife (236). In particular, shaft (226) is operable to distally advance and proximally retract along a longitudinal axis (230) such that motion of shaft (226) provides distal advancement and proximal retraction of staple driver (224) and knife (236).

Of course, any of these components may be varied in numerous ways as will be apparent to those of ordinary skill in the art in view of the teachings herein.

Drive assembly (200) is in further communication with a operator input (202) and a power source (204). Operator input (202) may include a manually actuated trigger (e.g., similar to trigger (74), etc.) and/or some other input operable to initiate motion of drive assembly (200). For instance, operator input (202) could include a button, trigger, lever, slider, touchpad, etc. that electrically initiates drive assembly (200). In addition or in the alternative, operator input (202) may include an electrical or software driven actuator operated by the operator to initiate motion of drive assembly (200). In some versions, operator input (202) may include a foot actuated pedal in communication with drive assembly (200). Other suitable forms that operator input (202) may take will be apparent to those of ordinary skill in the art in view of the teachings herein.

It will also be understood that operator input (202) may be placed in any appropriate position on or relative to circular surgical stapling instrument (10) as will be apparent to one of ordinary skill in the art in view of the teachings herein. For instance, operator input (202) may be positioned on any portion of actuator handle assembly (70) as seen in FIG. 1. Alternatively, operator input (202) may also be positioned somewhere separately from circular surgical stapling instrument (10), which may include locating operator input (202) on a separate console or computer. Operator input (202) could also be located on a console or device in wireless communication with circular surgical stapling instrument (10). Other suitable locations for operator input (202) will be apparent to those of ordinary skill in the art in view of the teachings herein.

Power source (204) may take a variety of forms. For instance, power source (204) may comprise an external source (e.g., wall outlet, etc.) coupled with instrument (10) by a cable. Power source (204) may also include a battery or battery pack (e.g., within instrument (10)) operable to deliver energy to drive assembly (200). Power source (204) in some instances may also provide a wirelessly induced energy operable to power drive assembly (200). Other suitable variations of power source (204) will be apparent to those of ordinary skill in the art in view of the teachings herein.

Drive assembly (200) of the present example comprises a motor (206), drive wheel (208), a vertical link (210), a first and second toggle link (216, 218), an anchor (220), and shaft (226). Motor (206) is in communication with operator input (202) and power source (204). Power source (204) is operable to provide electrical power to motor (206), to thereby drive motor (206). Operator input (202) is operable to initiate flow of power from power source (204) to motor (206) such that the operator may signal drive assembly (200) to start. Motor (206) may include any suitable kind of motor that is operable to provide rotational motion as would be apparent to one of ordinary skill in the art in view of the teachings herein.

Motor (206) is in communication with drive wheel (208). In particular, motor (206) is operable to rotate a drive shaft (240), which is unitarily coupled with drive wheel (208). Drive wheel (208) in the present example comprises a disc-shaped wheel. A longitudinal axis (228) extends through motor (206) and drive wheel (208) such that motor (206), drive shaft (240), and drive wheel (208) rotate coaxially about axis (228). Drive wheel (208) is in communication with vertical link (210) through a linking joint (242) and a first pin (212). Vertical link (210) is driven by drive wheel (208) in a reverse crankshaft fashion. In other words, linking joint (242) is mounted on drive wheel (208) such that as drive wheel (208) rotates, linking joint (242) and first pin (212) guide vertical link (210) to rise and fall in relation to axis (228). Linking joint (242) is offset from axis (228) such that linking joint (242) orbits about axis (228) when drive wheel (208) rotates. The point of contact between first pin (212) and vertical link (210) also orbits about longitudinal axis (228) when drive wheel (208) rotates. Linking joint (242) may be in communication with a first pin (212) through a ball and socket joint, a universal joint, or any other suitable connection operable to enable the lower end of vertical link (210) to follow an orbital path about longitudinal axis (228) as drive wheel (208) rotates. While pin (212) defines a relatively short distance between drive wheel (208) and vertical link (210) in the present example due to the overall length of linking joint (242), it will be appreciated that pin (212) may include a longer pin still operable to drive vertical link (210) upwardly and downwardly with the motion of drive wheel (208).

Vertical link (210) is in communication with a second pin (214), which is where vertical link (210) joins first toggle link (216) and second toggle link (218). It will be understood that vertical link (210) and second pin (214) may be in communication through a ball and socket joint, a universal joint, or any other suitable joint operable to allow vertical link (210) to pivot laterally relative to first and second toggle links as drive wheel (208) rotates. In the present example, first and second toggle links (216, 218) have a substantially similar construction, but it should be understood that other configurations may be used. For instance first and second toggle links (216, 218) may have different lengths, thicknesses, etc. Furthermore, the exemplary version shows first and second toggle links (216, 218) as having a straight construction, but it should be understood that first and second toggle links (216, 218) may also include angled or curved beams as well or other suitable constructions as would be apparent to one of ordinary skill in the art in view of the teachings herein. Likewise, in the exemplary version, the straight shape of vertical link (210) is substantially similar to first and second toggle links (216, 218), though it should be understood that vertical link (210) may have other configurations as well including a bent or curved shape. Other suitable configurations for links (210, 216, 218) will be apparent to those of ordinary skill in the art in view of the teachings herein.

Second toggle link (218) is in communication with anchor (220) such that second toggle link (218) can pivot in relation to anchor (220). In particular, a second toggle pin (246) couples anchor (220) with a portion of actuator handle assembly (70). However, it will be understood that anchor (220) may be affixed to any suitable portion of circular surgical stapling instrument (10) as would be apparent to one of ordinary skill in the art in view of the teachings herein. Furthermore, it will be understood that any suitable structure for pivotally coupling second toggle link (218) to anchor (220) may be used. Anchor (220) provides a fixed anchor point or mechanical ground for second toggle link (218), thereby preventing second toggle link (218) from translating relative to actuator handle assembly (70).

First toggle link (216) is in pivotal communication with shaft (226). In particular, a first toggle pin (248) pivotally couples first toggle link (216) to shaft (226). As a result, as vertical link (210) rises, second toggle link (218) and first toggle link (216) pivot in relation to anchor (220) and shaft (226), respectively, which aligns first and second toggle link (216, 218) with each other. This aligning causes shaft (226) to distally advance. A second longitudinal axis (230) extends through shaft (226). As vertical link (210) rises, first and second toggle links (216, 218) become more aligned with second longitudinal axis (230). At the peak of the upward motion of vertical link (210), first and second toggle links (216, 218) are substantially aligned with second longitudinal axis (230); and shaft (226) is in a distal-most position. As vertical link (210) travels downwardly, toggle links (216, 218) collapse and pull shaft (226) to a proximal-most position.

B. Exemplary Firing Sequence with Toggle Assembly

FIG. 7A shows drive assembly (200) in a pre-firing state. While drive assembly (200) is in this state, the operator may position circular surgical stapling instrument (10) within a severed, naturally occurring lumen within a patient in preparation for firing. Anvil (40) is drawn proximally relative to actuator handle assembly (70) from an initial, open position as shown in FIG. 2A to a closed position as shown in FIG. 2B, thereby reducing the gap distance d and the distance between the two portions of tissue to be joined. The distance d is controlled by manual rotation of adjusting knob (98). In the pre-firing state where anvil (40) is manually adjusted relative to stapling head assembly (20), motor (206) is idle and drive wheel (208) is at a rotational position such that pin (212) is the lowest in relation to first longitudinal axis (228), as shown in FIG. 7A. Accordingly, vertical link (210) is also at a low point in relation to first longitudinal axis (228). Furthermore, vertical link (210) is positioned substantially perpendicular to longitudinal axis (228). Toggle links (216, 218) are drawn toward first longitudinal axis (228) and are in a collapsed state. Shaft (226) is in a retracted state, and staple driver (224) and knife (236) are also retracted.

Figure 7B:
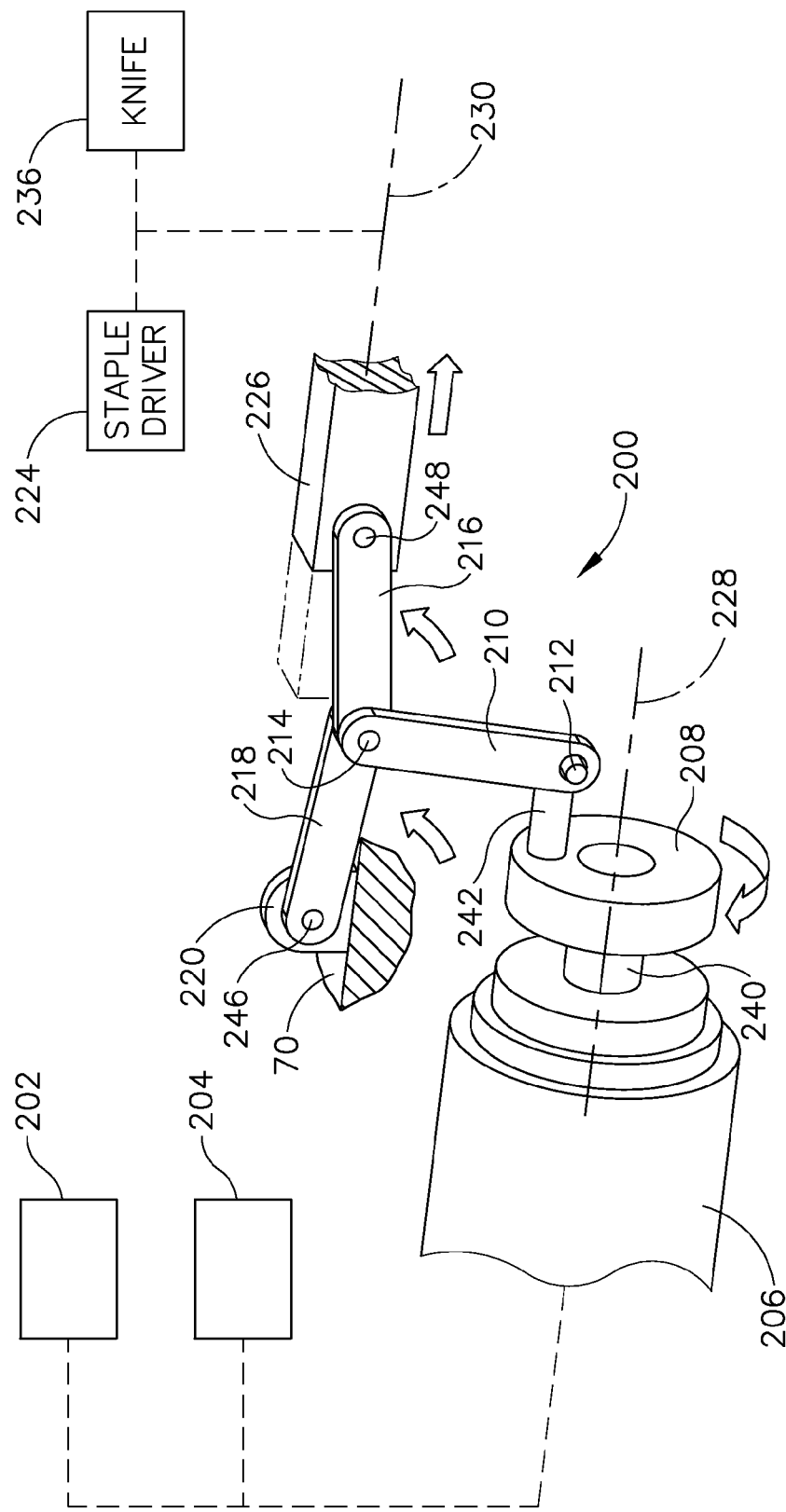
FIG. 7B depicts a side, perspective view of the drive assembly of FIG. 7A, in a mid-firing position with a vertical link urged upwardly.

Once the operator decides to fire circular surgical stapling instrument (10), the operator provides the command through operator input (202), which thereby causes power to be delivered by power source (204) to motor (206). Motor (206) is thus activated, thereby causing drive wheel (208) to turn as shown in FIG. 7B. As also seen in FIG. 7B, in a mid-firing state, drive wheel (208) has rotated a half revolution. Vertical link (210) is urged upwardly and toggle links (216, 218) straighten along second longitudinal axis (230). Vertical link (210) angles toward shaft (226). As toggle links (216, 218) straighten or substantially align with each other, shaft (226) advances distally. As shaft (226) advances distally, staple driver (224) and knife (236) also advance like staple driver (24) and knife (36) as previously described in relation to circular surgical stapling instrument (10). The distal motion of staple driver (224) and knife (236) drives staples (66) into tissue, forming an annular array at an anastomosis; while knife (236) severs excess tissue from the inner region of the annular array of deployed staples (66), similar to what is shown in FIG. 2C.

Figure 10:
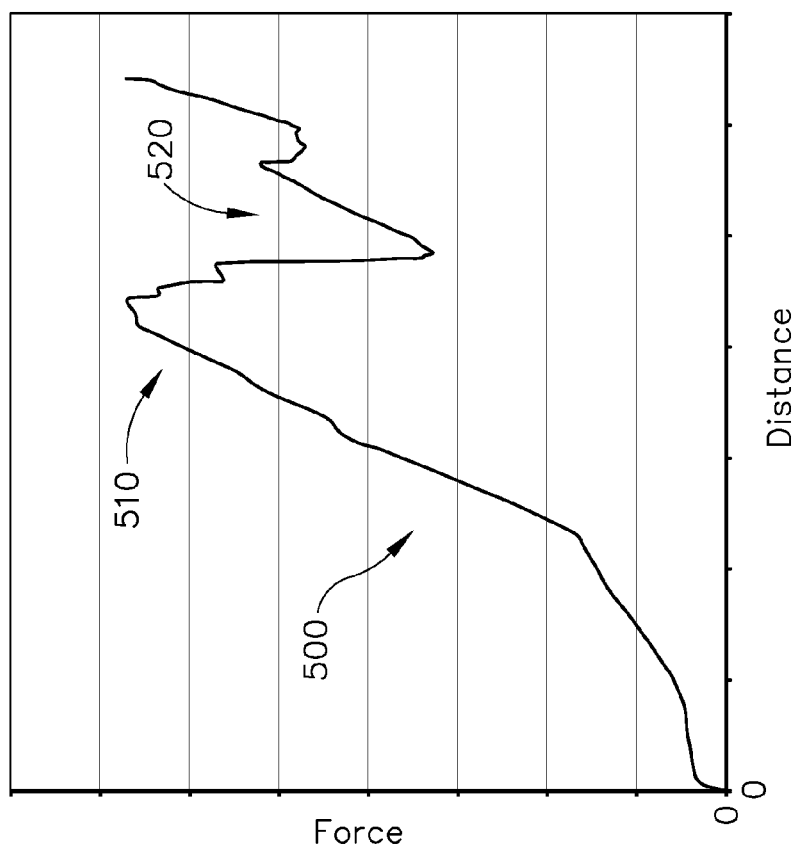
FIG. 10 depicts an exemplary force profile associated with a firing stroke for a circular stapling surgical instrument.

In some versions, anvil (40) as seen in FIG. 2A contains a breakable washer that is broken by knife (236) when knife (236) completes a full distal range of motion. The washer is thus configured to provide an audible or haptic feedback through actuator handle assembly (70) as the washer breaks in response to completion of full advancement of knife (236) toward anvil (40). It should be understood that the presence of the washer may present a sudden increase in the force required to advance knife (236) distally. FIG. 10 shows an exemplary force profile encountered by knife (236) during the range of distal travel of knife (236). In a first range (500) of distal motion, knife (236) encounters a gradually increasing load or resisting force as knife (236) passes through tissue (2). In a second range (510) of distal motion, knife (236) encounters a spike in load or resisting force as knife (236) passes through the washer. In a third range (520) of distal motion, knife (236) first encounters a sudden drop in load or resisting force after the washer breaks, then a subsequent increase in load or resisting force as knife (236) engages a proximally facing surface of anvil (40). In view of the foregoing, it should be further understood that during the transition from the position shown in FIG. 7A to the position shown in FIG. 7B, toggle links (216, 218) provide an increasing mechanical advantage as knife (236) approaches the end of its distal range of movement (e.g., beginning during the second range (520) of distal motion), thereby providing greater distal driving force by which to break the washer. Of course, in some versions, the washer may be omitted entirely.

Motor (206) continues to drive wheel (208) in the same rotational direction, as seen in FIG. 7C, where drive wheel (208) has made a full revolution, returning to the same rotational position as was shown in FIG. 7A. Vertical link (210) is pulled downwardly by rotation of drive wheel (208) from the position shown in FIG. 7B to the position shown in FIG. 7C. As vertical link (210) pulls downwardly, toggle links (216, 218) collapse and pull shaft (226) proximally. A full firing stroke of drive assembly (200) is thus completed. The operator may then remove circular surgical stapling instrument (10) from the surgical site.

It will be appreciated that power source (204) or motor (206) may be configured to only allow a single revolution of drive wheel (208), which represents a complete actuation. For a single 360 degree rotation, drive assembly (200) may be configured such that shaft (226) distally advances for the first 180 degrees of drive wheel (208) rotation; while shaft (226) proximally retracts for the second 180 degrees of drive wheel (208) rotation. In some instances, a microcontroller, ASIC, and/or other type of control module is in communication with power source (204) and motor (206) and is configured to automatically stop motor (206) thereby providing a way to dynamically brake motor (206) such that motor (206) may be actuated for exactly one rotation of drive wheel (208). By way of example only, such a control module may be in communication with an encoder that is in communication with shaft (240). As another merely illustrative example, such a control module may be in communication with one or more reed switches that are in communication with shaft (226). Other suitable types of sensors and control modules that may be used to provide precise stopping of motor (206) (e.g., based on tracked rotation of drive wheel (208), based on translation of shaft (240), and/or based on some other parameter, etc.) will be apparent to those of ordinary skill in the art in view of the teachings herein. Of course, a control module may be configured to control motor (206) to activate for any suitable number of rotations, etc. In some instances, controlling the starting and stopping of motor (206) may be performed in accordance with the teachings of U.S. patent application Ser. No. 14/033,751, entitled CONTROL FEATURES FOR MOTORIZED SURGICAL STAPLING INSTRUMENT, filed on even date herewith, published as U.S. Pub. No. 2015/0083774 on Mar. 26, 2015, now U.S. Pat. No. 9,907,552, issued on Mar. 6, 2018, the disclosure of which is incorporated by reference herein.

C. Exemplary Drive Assembly with Angled Cam

Figure 8:
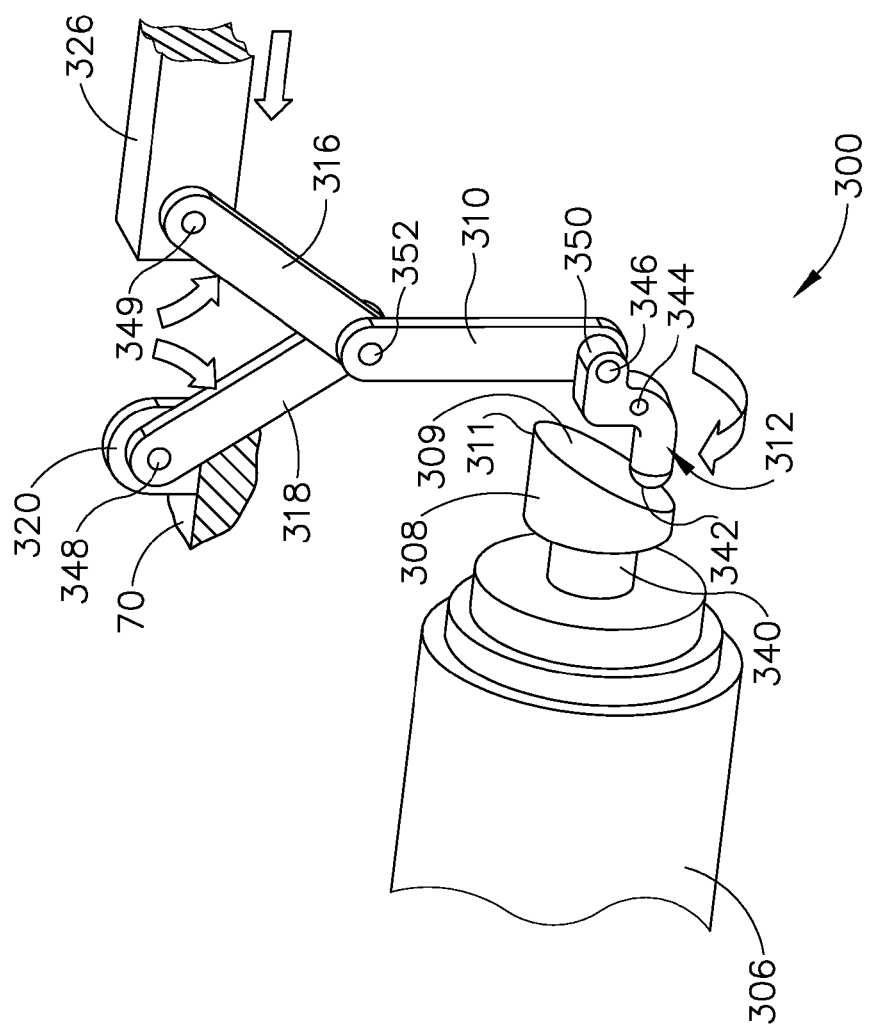
FIG. 8 depicts a side, perspective view of another exemplary alternative drive assembly for use with the circular stapling surgical instrument of FIG. 1, featuring an angled cam shaft.

FIG. 8 shows an exemplary alternative drive assembly (300) that may be used or incorporated with circular surgical stapling instrument (10) to provide motorized driving of staples (66) and knife (36). In particular, drive assembly (300) of this example comprises a motor (306), an angled cam (308), a cam follower (312), a vertical link (310), a first toggle link (316), a second toggle link (318), an anchor (320), and a shaft (326). Motor (306), vertical link (310), first toggle link (316), second toggle link (318), anchor (320), and shaft (326) are substantially similar to motor (206), vertical link (210), first toggle link (216), second toggle link (218), anchor (220), and shaft (226) described above. Similar to motor (206), motor (306) may be controlled in accordance with the teachings of U.S. patent application Ser. No. 14/033,751, entitled CONTROL FEATURES FOR MOTORIZED SURGICAL STAPLING INSTRUMENT, filed on even date herewith, published as U.S. Pub. No. 2015/0083774 on Mar. 26, 2015, now U.S. Pat. No. 9,907,552, issued on Mar. 6, 2018, the disclosure of which is incorporated by reference herein. Vertical link (310) is in pivotal communication with first and second toggle links (316, 318) through first pivot pin (352). First toggle link (316) is in communication with shaft (326) through second pivot pin (349). Second toggle link (318) is in communication with anchor (320) through third pivot pin (348).

Angled cam (308) is rotationally coupled to motor (306) through drive shaft (340). Angled cam (308) has an angled distal surface (309) in contact with cam follower (312). In particular, cam follower (312) has a proximal free end (342), which maintains contact with angled surface (309) as angled cam (308) rotates. Distal surface (309) is obliquely angled in relation to the axis of drive shaft (340), such that distal surface (309) will drive free end (342) distally as cam (308) is rotated from the position shown in FIG. 8 to a position that is 180 degrees from the position of cam (308) shown in FIG. 8. Cam follower (312) is pivotally secured to a pivot pin (344). Pivot pin (344) is coupled with any suitable portion of actuator handle assembly (70) thereby providing a mechanical ground about which cam follower (312) can pivot. Cam follower (312) also includes a connection pin (346) that couples a distal end (350) of cam follower (312) to vertical link (310). As a result, cam follower (312) and vertical link (310) are operable to pivot about connection pin (346). Pivot pin (344) is positioned between distal end (350) and proximal free end (342) of cam follower (312).

Angled cam (308) and cam follower (312) cooperate to raise and lower vertical link (310) by causing cam follower (312) to pivotally rock about pivot pin (344). In the stage of operation shown in FIG. 8, shaft (326) is in a retracted proximal position, such that staple driver (24) and knife (36) are in a retracted proximal position. Toggle links (316, 318) are in a collapsed configuration and vertical link (310) is in a lower position. Proximal free end (342) of cam follower (312) is in contact with a proximal-most region of angled distal surface (309). When motor (306) is activated to rotate angled cam (308) through the first half of a full revolution, a distal-most region (311) of angle distal surface (309) bears against proximal free end (342) of cam follower (312), thereby driving proximal free end (342) distally. This causes cam follower (312) to rotate counterclockwise about pivot pin (344). Distal end (350) of cam follower (312) is accordingly urged upwardly, which raises vertical link (310) upwardly. As vertical link (310) raises upwardly, first and second toggle links (316, 318) straighten or substantially align with each other, thereby driving shaft (326) distally. This drives staple driver (24) and knife (36) distally, thereby stapling tissue at an anastomosis site and cutting away excess tissue within the anastomosis as described above.

In some versions, cam follower (312) is constructed of slidably moving components such that distal end (350) extends distally from pivot pin (344) when cam follower (312) rotates counter clockwise, thereby allowing distal end (350) to fully raise vertical link (310). Such slidably moving components may be configured to enable vertical link (310) to maintain a vertical orientation as cam follower (312) rotates about pivot pin (344), while still providing vertical movement of vertical link (310) in response to rotation of cam follower (312). In addition or in the alternative, cam follower (312) may define an elongate slot to receive connection pin (346). Such a slot may be configured to enable vertical link (310) to maintain a vertical orientation as cam follower (312) rotates about pivot pin (344), while still providing vertical movement of vertical link (310) in response to rotation of cam follower (312). It should also be understood that that the movement of shaft (326) may also be controlled in accordance with the teachings of U.S. patent application Ser. No. 14/033,668, entitled SURGICAL STAPLER WITH ROTARY CAM DRIVE AND RETURN, filed on even date herewith, published as U.S. Pub. No. 2015/0083772 on Mar. 26, 2015, the disclosure of which is incorporated by reference herein.

As motor (306) continues to drive angled cam (308) through the second half of a full revolution, shaft (326) returns back to the proximal position shown in FIG. 8. Toggle links (316, 318) return back to the collapsed state; vertical link (310) returns to a downward position; and cam follower (312) is rotated clockwise. In the present example, a resilient member (e.g., coil spring, etc.) resiliently biases shaft (326) back toward the proximal position. In addition or in the alternative, one or more torsion springs may be positioned about pin (348) and/or pin (349) to resiliently bias links (310, 316) to the position shown in FIG. 8. In addition or in the alternative, a torsion spring may be positioned about pin (344) to resiliently bias cam follower (312) to the position shown in FIG. 8. It should be understood that, during the second half of the full revolution of angled cam (308), proximal free end (342) of cam follower (312) transitions from engaging the distal-most region (311) of angled distal surface (309) to engaging the proximal-most region of angled distal surface (309). This transition enables cam follower (312) to rotate clockwise back to the position shown in FIG. 8, as the angled configuration of angled distal surface (309) provides clearance for such rotation.

In some versions, motor (306) and/or shaft (326) may be in communication with one or more sensors (e.g., encoder, reed switch, etc.) that are operable to track rotation of cam (308) and/or the displacement of shaft (326). Such information may be communicated to or displayed to a control unit in communication with instrument (10) for use by the operator. In addition or in the alternative, such information may be processed by a control module, which may automatically stop motor (306) (e.g., using dynamic braking, etc.) upon completion of a full 360 degrees of rotation of cam (308). Various suitable types of sensors and control modules that may be used to provide precise stopping of motor (306) will be apparent to those of ordinary skill in the art in view of the teachings herein. Of course, a control module may be configured to control motor (306) to activate for any suitable number of rotations, etc. In some instances, controlling the starting and stopping of motor (306) may be performed in accordance with the teachings of U.S. patent application Ser. No. 14/033,751, entitled CONTROL FEATURES FOR MOTORIZED SURGICAL STAPLING INSTRUMENT, filed on even date herewith, published as U.S. Pub. No. 2015/0083774 on Mar. 26, 2015, now U.S. Pat. No. 9,907,552, issued on Mar. 6, 2018, the disclosure of which is incorporated by reference herein.

D. Exemplary Drive Assembly with Rack and Pinion

Figure 9:
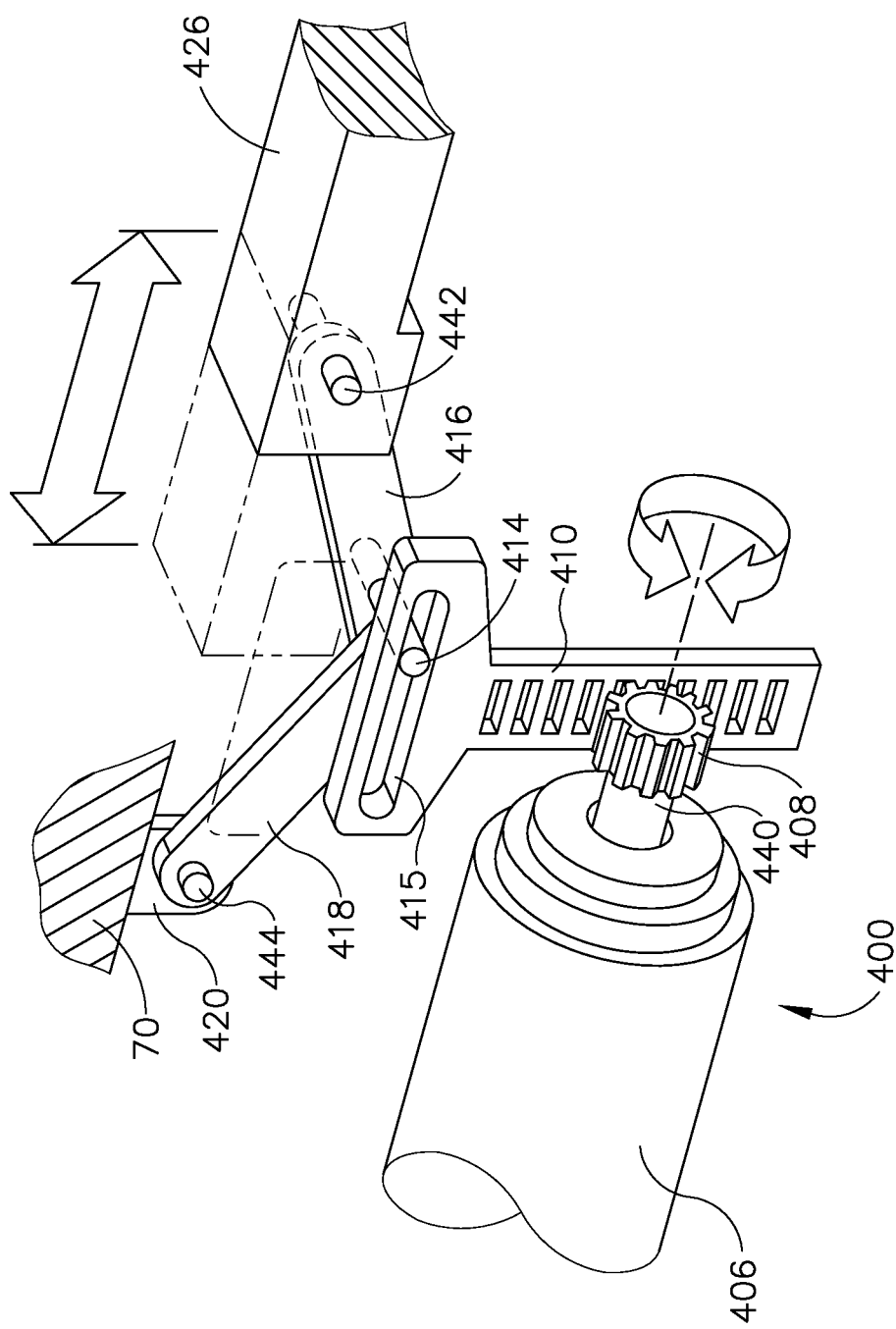
FIG. 9 depicts a side, perspective view of yet another exemplary alternative drive assembly for use with the circular stapling surgical instrument of FIG. 1, featuring a rack and pinion mechanism.

FIG. 9 shows another exemplary alternative drive assembly (400) operable for use with circular surgical stapling instrument (10) for driving staple driver (24) and knife (36). Drive assembly (400) of this example comprises a motor (406), a drive pinion (408), a rack (410), a first toggle link (416), a second toggle link (418), an anchor (420), and a shaft (426). Motor (406), first toggle link (416), second toggle link (418), anchor (420), and shaft (426) are substantially similar to motor (206), vertical link (210), first toggle link (216), second toggle link (218), anchor (220), and shaft (226) described above. Similar to motor (206), motor (406) may be controlled in accordance with the teachings of U.S. patent application Ser. No. 14/033,751, entitled CONTROL FEATURES FOR MOTORIZED SURGICAL STAPLING INSTRUMENT, filed on even date herewith, published as U.S. Pub. No. 2015/0083774 on Mar. 26, 2015, now U.S. Pat. No. 9,907,552, issued on Mar. 6, 2018, the disclosure of which is incorporated by reference herein.

Motor (406) is in communication with drive pinion (408) through a drive shaft (440) such that motor (406) drives pinion (408) to rotate. Drive pinion (408) is in communication with rack (410) such that rotation of drive pinion (408) raises and lowers rack (410). Motor (406) of the present example is operable to rotate in forward and reverse in order to facilitate the raising and lowering and lowering of rack (410). In particular, if motor (406) rotates in one direction, rack (410) raises upwardly, and if motor (406) rotates in the opposite direction, rack (410) lowers downwardly. An upper portion of rack (410) defines a horizontal slot (415). Rack (410) is in communication with toggle links (416, 418) through a pin (414), which is disposed in slot (415). In particular, pin (414) is operable to slide horizontally through slot (415). Toggle link (416) is in communication with shaft (426) through a second pin (442), while toggle link (418) is in communication with anchor (420) through third pin (444).

Rotation of drive pinion (408) causes shaft (426) to advance and retract to drive a staple driver (24) or knife (36). In particular, when motor (406) rotates pinion (408) in a first direction to drive rack (410) upwardly, toggle links (416, 418) straighten or substantially align with each other and thereby advance shaft (426) distally. This drives staple driver (24) and knife (36) distally, thereby stapling tissue at an anastomosis site and cutting away excess tissue within the anastomosis as described above. When motor (406) rotates pinion (408) in a second direction to drive rack (410)

downwardly, toggle links (416, 418) collapse and thereby retract shaft (426) proximally. Slot (415) accommodates horizontal movement of pin (414) as rack (410) raises and lowers.

It will be understood that different ways of reversing motor (406) could be utilized. For instance, motor (406) could be in communication with a microcontroller, ASIC, and/or other type of control module that is configured to selectively reverse motor (406) and stop motor (406). Motor (406) could also be controlled in accordance with the teachings of U.S. patent application Ser. No. 14/033,751, entitled CONTROL FEATURES FOR MOTORIZED SURGICAL STAPLING INSTRUMENT, filed on even date herewith, published as U.S. Pub. No. 2015/0083774 on Mar. 26, 2015, now U.S. Pat. No. 9,907,552, issued on Mar. 6, 2018, the disclosure of which is incorporated by reference herein. The control module may be in communication with one or more sensors (e.g., encoder, reed switch, etc.) that are operable to track rotation of pinion (408) and/or the displacement of shaft (426). Such information may be processed by the control module, which may automatically reverse motor (406) upon completion of full distal advancement of shaft (426); and then stop motor (406) (e.g., using dynamic braking, etc.) upon completion of full proximal retraction of shaft (426). Other suitable ways in which motor (406) could be controlled will be apparent to those of ordinary skill in the art in view of the teachings herein.

As yet another merely illustrative example, drive assembly (400) may be configured such that motor (406) rotates drive shaft (440) in just one single direction in order to both advance and retract shaft (426). For instance, motor (406) may rotate drive shaft (440) in a first rotational direction to drive rack (410) through a first range of upward motion to advance shaft (426) distally via toggle links (416, 418). Shaft (426) may reach a distal-most position when both toggle links (416, 418) are horizontally oriented. As motor (406) continues to rotate drive shaft (440) in the first rotational direction, thereby driving rack (410) through a second range of upward motion, rack (410) may cause toggle links (416, 418) to again collapse, thereby retracting shaft (426) proximally. Shaft (426) may thus be advanced and retracted without having to reverse the direction of drive shaft (440) rotation.

III. Miscellaneous

In the examples shown in FIGS. 7-9, motors (206, 306, 406) are oriented coaxially with drive shafts (240, 340, 440) and parallel to shafts (226, 326, 426). However, motors (206, 306, 406) may instead positioned in other suitable orientations. For instance, in some versions, motors (206, 306, 406) may be positioned perpendicularly or at any oblique angle in relation to a longitudinal axis of drive shafts (240, 340, 440) and/or shafts (226, 326, 426). In some such versions, motors (206, 306, 406) may be positioned within a pistol grip provided by an alternative version of handle assembly (70). Motors (206, 306, 406) may be configured to convey rotational movement along non-parallel axes by coupling motors (206, 306, 406) to shafts (240, 340, 440) through bevel gears, etc.; and/or using any other suitable structure(s). By way of example only, motors (206, 306, 406) may transfer motion to drive shafts (240, 340, 440) in accordance with the teachings of U.S. patent application Ser. No. 14/033,668, entitled SURGICAL STAPLER WITH ROTARY CAM DRIVE AND RETURN, filed on even date herewith, published as U.S. Pub. No. 2015/0083772 on Mar. 26, 2015, the disclosure of which is incorporated by reference herein.

Similarly, handle assembly (70) may provide a perpendicularly oriented or obliquely oriented pistol grip in accordance with the teachings of U.S. patent application Ser. No. 14/033,668, entitled SURGICAL STAPLER WITH ROTARY CAM DRIVE AND RETURN, filed on even date herewith, published as U.S. Pub. No. 2015/0083772 on Mar. 26, 2015, the disclosure of which is incorporated by reference herein. Other suitable ways in which obliquely oriented motors (206, 306, 406) may be incorporated into the instruments described herein will be apparent to those of ordinary skill in the art in view of the teachings herein.

While the examples herein have been provided in the context of a circular stapling instrument, it should be understood that the various teachings herein may be readily applied to various other kinds of surgical instruments. By way of example only, the various teachings herein may be readily applied to linear stapling devices (e.g., endocutters). For instance, various teachings herein may be readily combined with various teachings of U.S. Pub. No. 2012/0239012, entitled "Motor-Driven Surgical Cutting Instrument with Electric Actuator Directional Control Assembly," published Sep. 20, 2012, now U.S. Pat. No. 8,453,914, issued on Jun. 4, 2013, the disclosure of which is incorporated by reference herein, and/or U.S. Pub. No. 2010/0264193, entitled "Surgical Stapling Instrument with An Articulatable End Effector," published Oct. 21, 2010, now U.S. Pat. No. 8,408,439, issued on Apr. 2, 2013, the disclosure of which is incorporated by reference herein, as will be apparent to those of ordinary skill in the art. As another merely illustrative example, the various teachings herein may be readily applied to a motorized electrosurgical device. For instance, various teachings herein may be readily combined with various teachings of U.S. Pub. No. 2012/0116379, entitled "Motor Driven Electrosurgical Device with Mechanical and Electrical Feedback," published May 10, 2012, now U.S. Pat. No. 9,161,803, issued on Oct. 20, 2015, the disclosure of which is incorporated by reference herein, as will be apparent to those of ordinary skill in the art. Other suitable kinds of instruments in which the teachings herein may be applied, and various ways in which the teachings herein may be applied to such instruments, will be apparent to those of ordinary skill in the art.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

At least some of the teachings herein may be readily combined with one or more teachings of U.S. Pat. No. 7,794,475, entitled "Surgical Staples Having Compressible or Crushable Members for Securing Tissue Therein and Stapling Instruments for Deploying the Same," issued Sep. 14, 2010, the disclosure of which is incorporated by reference herein; U.S. patent application Ser. No. 13/693,430, entitled "Trans-Oral Circular Anvil Introduction System with Dilation Feature," filed Dec. 4, 2012, now U.S. Pat. No. 9,572,573, issued on Feb. 21, 2017, the disclosure of which is incorporated by reference herein; U.S. patent application Ser. No. 13/688,951, entitled "Surgical Staple with Integral Pledget for Tip Deflection," filed Nov. 29, 2012, now U.S.

Pat. No. 9,289,207, issued on Mar. 22, 2016, the disclosure of which is incorporated by reference herein; U.S. patent application Ser. No. 13/706,827, entitled "Surgical Stapler with Varying Staple Widths along Different Circumferences," filed Dec. 6, 2012, published as U.S. Pub. No. 2014/0158747 on Jun. 12, 2014, the disclosure of which is incorporated by reference herein; U.S. patent application Ser. No. 13/688,992, entitled "Pivoting Anvil for Surgical Circular Stapler," filed Nov. 29, 2012, now U.S. Pat. No. 9,498,222, issued on Nov. 22, 2016, the disclosure of which is incorporated by reference herein; U.S. patent application Ser. No. 13/693,455, entitled "Circular Anvil Introduction System with Alignment Feature," filed Dec. 4, 2012, now U.S. Pat. No. 9,724,100, issued on Aug. 8, 2017, the disclosure of which is incorporated by reference herein; U.S. patent application Ser. No. 13/716,313, entitled "Circular Stapler with Selectable Motorized and Manual Control, Including a Control Ring," filed Dec. 17, 2012, now U.S. Pat. No. 9,532,783, issued on Jan. 3, 2017, the disclosure of which is incorporated by reference herein; U.S. patent application Ser. No. 13/716,318, entitled "Motor Driven Rotary Input Circular Stapler with Modular End Effector," filed Dec. 17, 2012, now U.S. Pat. No. 9,597,081, issued on Mar. 21, 2017, the disclosure of which is incorporated by reference herein; and/or U.S. patent application Ser. No. 13/716,323, entitled "Motor Driven Rotary Input Circular Stapler with Lockable Flexible Shaft," filed Dec. 17, 2012, issued as U.S. Pat. No. 9,463,022 on Oct. 1, 2016, the disclosure of which is incorporated by reference herein. Various suitable ways in which such teachings may be combined will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus, comprising:
   (a) an end effector comprising a staple driver, wherein the staple driver is operable to distally advance along the end effector;
   (b) a shaft assembly including a translatable drive member in communication with the staple driver; and
   (c) a drive assembly in communication with the translatable drive member, wherein the drive assembly comprises:
      (i) a motor,
      (ii) a rotary drive member in communication with the motor,
      (iii) a first link in communication with the rotary drive member, and
      (iv) at least one toggle link in communication with the first link, wherein the at least one toggle link is also in communication with the translatable drive member, wherein the at least one toggle link is rotatable relative to the translatable drive member;
   wherein the rotary drive member is configured to induce linear motion in the first link, wherein the first link is configured to convey linear motion to the at least one toggle link that is non-parallel to the linear motion of the first link, wherein the at least one toggle link is configured to convey linear motion to the translatable drive member.

2. The apparatus of claim 1, wherein the rotary drive member and the first link are in communication through a pin, wherein the pin is offset from the center of the rotary drive member.

3. The apparatus of claim 1, wherein the drive assembly further comprises a cam follower, wherein the rotary drive member comprises an angled surface, wherein the rotary drive member and the first link are in communication through the cam follower, wherein the rotary drive member is operable to move the cam follower through a camming motion.

4. The apparatus of claim 3, wherein the cam follower is pivotally coupled to a mechanical ground.

5. The apparatus of claim 1, wherein the rotary drive member is configured to rotate half a revolution to raise the first link, wherein the first link is operable to fully advance the translating drive member in response to a half revolution of the rotary drive member.

6. The apparatus of claim 1, wherein the rotary drive member is configured to raise and lower the first link with a full revolution, wherein the first link is operable to fully advance and fully retract the translating drive member with a full revolution of the rotary drive member.

7. The apparatus of claim 1, wherein the motor defines a longitudinal axis, wherein the first link is positioned substantially perpendicular to the longitudinal axis.

8. The apparatus of claim 1, wherein the at least one toggle link comprises a first toggle link and a second toggle link.

9. The apparatus of claim 8, wherein the second toggle link is pivotally affixed to an anchor point.

10. The apparatus of claim 9, wherein the first toggle link is pivotally coupled with the translating drive member.

11. The apparatus of claim 10, wherein the first toggle link and the second toggle link are in communication with the first link through a single pivot point, wherein the first toggle link and the second toggle link are operable to form straightened configuration to advance the translating drive member distally, wherein the first toggle link and the second toggle link are operable to form a collapsed configuration to retract the translating drive member proximally.

12. The apparatus of claim 11, wherein the shaft defines a longitudinal axis, wherein the first toggle link and the second toggle link are operable to selectively align parallel to the longitudinal axis.

13. The apparatus of claim 1, wherein the drive assembly is operable to provide a variable mechanical advantage to the translatable driver during a range of distal travel by the translatable driver.

14. The apparatus of claim 1, wherein the rotary drive member comprises a drive pinion, wherein the first link comprises a rack.

15. The apparatus of claim 14, wherein the drive assembly further comprises a pin in communication with the at least one toggle link, wherein the rack defines a slot, wherein the pin is slidably disposed in the slot.

16. An apparatus comprising:
(a) an end effector comprising a staple driver operable to translate relative to the rest of the end effector;
(b) a shaft assembly including a translatable drive member in communication with the staple driver; and
(c) a drive assembly operable to translate the translatable drive member and the staple driver, wherein the drive assembly comprises:
  (i) a motor,
  (ii) a rotary member coupled to the motor, wherein the motor is operable to rotate the rotary member relative to the shaft assembly, and
  (iii) a linkage assembly operable to rotate and translate in response to rotation of the rotary member in order to drive the translatable drive member, wherein the linkage assembly comprises:
    (A) a first link in communication with the rotatory member, wherein the rotatory member is configured to rotate and translate the first link, and
    (B) a toggle link rotationally coupled to the first link and the translatable drive member, wherein the first link is configured to rotate the toggle link relative to the first link and the translatable drive member in order to linearly drive the translatable drive member.

17. An apparatus, comprising:
(a) a body;
(b) an end effector comprising a staple driver, wherein the staple driver is operable to distally advance along the end effector;
(c) a shaft assembly extending between the body and the end effector, wherein the shaft assembly includes a translatable drive member in communication with the staple driver; and
(d) a drive assembly in communication with the translatable drive member, wherein the drive assembly comprises:
  (i) a motor,
  (ii) a rotary drive member in communication with the motor,
  (iii) a first link in communication with the rotary drive member, and
  (iv) a plurality of toggle links, wherein the plurality of toggle links comprises:
    (A) a first toggle link in communication with the first link, wherein the first toggle link is also in communication with the translatable drive member, and
    (B) a second toggle link, wherein the second toggle link is pivotally coupled to the first toggle link, wherein the second toggle link is pivotally affixed to an anchor point, wherein the anchor point is fixed relative to the body;
  wherein the rotary drive member is configured to induce linear motion in the first link, wherein the first link is configured to convent rotational motion to the second toggle link, wherein the first link is configured to convey linear motion to the first toggle link that is non-parallel to the linear motion of the first link, wherein the at least one toggle link is configured to convey linear motion to the translatable drive member.

18. The apparatus of claim 17, wherein the rotary drive member comprises a camming surface.

19. The apparatus of claim 17, wherein the rotary drive member comprises a spur gear and the first link comprises a rack.

20. The apparatus of claim 17, wherein the rotary drive member comprises a linking joint.

* * * * *